US012643859B2

(12) United States Patent
Lian et al.

(10) Patent No.: US 12,643,859 B2
(45) **Date of Patent: *Jun. 2, 2026**

(54) PYRIDYL OXYCARBOXYLIC ACID OXIME DERIVATIVE AND PREPARATION METHOD THEREFOR, WEEDING COMPOSITION AND APPLICATION THEREOF

(71) Applicant: Qingdao Kingagroot Chemical Compound Co., Ltd., Qingdao (CN)

(72) Inventors: Lei Lian, Qingdao (CN); Xuegang Peng, Qingdao (CN); Rongbao Hua, Qingdao (CN); Jingyuan Zhang, Qingdao (CN); Qi Cui, Qingdao (CN)

(73) Assignee: Qingdao Kingagroot Chemical Compound Co., Ltd., Qingdao (CN)

( * ) Notice: Subject to any disclaimer, the term of this patent is extended or adjusted under 35 U.S.C. 154(b) by 968 days.

This patent is subject to a terminal disclaimer.

(21) Appl. No.: 17/414,455

(22) PCT Filed: Dec. 20, 2019

(86) PCT No.: PCT/CN2019/126799

§ 371 (c)(1),
(2) Date: Jun. 16, 2021

(87) PCT Pub. No.: WO2020/135236

PCT Pub. Date: Jul. 2, 2020

(65) Prior Publication Data

US 2022/0064115 A1 Mar. 3, 2022

(30) Foreign Application Priority Data

Dec. 27, 2018 (CN) ......................... 201811609342.8

(51) Int. Cl.
*C07D 213/73* (2006.01)
*A01N 43/40* (2006.01)
*C07D 405/12* (2006.01)

(52) U.S. Cl.
CPC ........... *C07D 213/73* (2013.01); *A01N 43/40* (2013.01); *C07D 405/12* (2013.01)

(58) Field of Classification Search
CPC ...................................................... C07D 213/73
See application file for complete search history.

(56) References Cited

U.S. PATENT DOCUMENTS

| | | | | |
|---|---|---|---|---|
| 3,755,339 A * | 8/1973 | McKendry | C07D 213/73 546/297 |
| 3,761,486 A * | 9/1973 | McGregor | C07D 213/73 546/297 |
| 4,108,629 A | 8/1978 | McKendry | |
| 5,013,659 A | 5/1991 | Bedbrook et al. | |
| 5,698,539 A | 12/1997 | Ziemer et al. | |

FOREIGN PATENT DOCUMENTS

| | | |
|---|---|---|
| CN | 104803987 | 7/2015 |
| CN | 104803987 A * | 7/2015 |
| CN | 106187872 | 12/2016 |
| DE | 2335349 | 1/1975 |
| EP | 0131624 | 1/1985 |
| EP | 0142924 | 5/1985 |
| EP | 0193259 | 9/1986 |
| EP | 0221044 | 5/1987 |

(Continued)

OTHER PUBLICATIONS

NIH "Fluroxypyr" 2024, National Library of Medicine, PubChem, https://pubchem.ncbi.nlm.nih.gov/compound/Fluroxypyr (accessed Aug. 28, 2024) (Year: 2024).*
NIH "Quinclorac" 2024, National Library of Medicine, PubChem, https://pubchem.ncbi.nlm.nih.gov/compound/Quinclorac (accessed Aug. 28, 2024) (Year: 2024).*
Jhala "2017 Chart for Selection of Herbicides Based on Site of Action" Feb. 2, 2017, University of Nebraska-Lincoln CropWatch, https://cropwatch.unl.edu/2017/2017-chart-selection-herbicides-based-site-action (accessed Aug. 28, 2024) (Year: 2017).*

(Continued)

*Primary Examiner* — Bethany P Barham
*Assistant Examiner* — Judith Marie Kamm
(74) *Attorney, Agent, or Firm* — FINNEGAN, HENDERSON, FARABOW, GARRETT & DUNNER LLP

(57) ABSTRACT

The invention relates to the field of pesticide technology, and in particular a type of pyridyloxy carboxylic oxime derivative, preparation method, herbicidal composition and application thereof. The pyridyloxy carboxylic oxime derivative is represented by formula I,

I

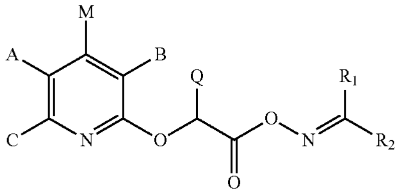

wherein, A, B each independently represent halogen, or alkyl or cycloalkyl with or without halogen; C represents hydrogen, halogen, alkyl or haloalkyl; Q represents halogen, cyano, cyanoalkyl, hydroxyalkyl, amino, nitro, formyl, alkyl with or without halogen and the like; $R_1$ and $R_2$ independently represent hydrogen, halogen, cyano, nitro, alkyl, haloalkyl, alkenyl, cycloalkyl, alkoxy, acyloxy, alkylthio, or unsubstituted or substituted aryl, etc.; M represents nitro or $NR_3R_4$. The compound has excellent herbicidal activity and higher crop safety, especially good selectivity for key crops such as rice.

12 Claims, No Drawings

(56) References Cited

FOREIGN PATENT DOCUMENTS

| | | | |
|---|---|---|---|
| EP | 0242236 | | 10/1987 |
| EP | 0242246 | | 10/1987 |
| EP | 0257993 | | 3/1988 |
| GB | 1418979 | | 12/1975 |
| JP | S62238266 | A | * 10/1987 |
| JP | 5393655 | B2 | 1/2014 |
| WO | WO91/13972 | | 9/1991 |
| WO | WO91/19806 | | 12/1991 |
| WO | WO92/00377 | | 1/1992 |
| WO | WO92/11376 | | 7/1992 |
| WO | WO92/14827 | | 9/1992 |

OTHER PUBLICATIONS

Christou P, Transformation Technology, *Trends in Plant Science*, 1:423-431 (1996).

Braun et al., The General Mitochondrial Processing Peptidase from Potato is an Integral Part of Cytochrome C Reductase of The Respiratory Chain, *EMBO J.* 11:3219-3227 (1992).

Wolter et al., Rbcs Genes in Solanum Tuberosum: Conservation of Transit Peptide and Exon Shuffling During Evolution, *Proc. Natl. Acad. Sci. USA*, 85:846-850 (1988).

Sonnewald et al., Transgenic Tobacco Plants Expressing Yeast-Derived Invertase in Either the Cytosol, Vacuole or Apoplast: A Powerful Tool for Studying Sucrose Metabolism and Sink/Source Interactions, *Plant J.* 1:95-106 (1991).

International Search Report for International Application No. PCT/CN2019/126799 dated Mar. 17, 2020.

Written Opinion for International Application No. PCT/CN2019/126799 dated Mar. 17, 2020.

* cited by examiner

PYRIDYL OXYCARBOXYLIC ACID OXIME DERIVATIVE AND PREPARATION METHOD THEREFOR, WEEDING COMPOSITION AND APPLICATION THEREOF

TECHNICAL FIELD

The invention relates to the field of pesticide technology, and in particular a type of pyridyloxy carboxylic oxime derivative, preparation method, herbicidal composition and application thereof.

TECHNICAL BACKGROUND

Weed control is one of the most important links in the course of achieving high-efficiency agriculture. Various herbicides are available in the market, for example, DE2335349A1, GB1418979A, U.S. Pat. Nos. 3,761,486, 3,755,339 and the like disclose a series of compounds represented by the general formula

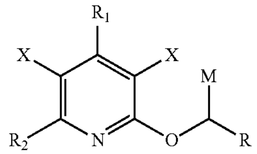

and application thereof as herbicides. However, scientists still need to do continuously research and develop new herbicides with high efficacy, safety, economics and different modes of action due to problems such as the growing market, weed resistance, the service life and economics of pesticides as well as people's increasing concern on environment.

Invention Contents

The present invention provides a type of pyridyloxy carboxylic oxime derivative, preparation method, herbicidal composition and application thereof. The compound has excellent herbicidal activity and higher crop safety, especially good selectivity for key crops such as rice.

The technical solution adopted by the invention is as follows:

A pyridyloxy carboxylic oxime derivative represented by formula I,

I

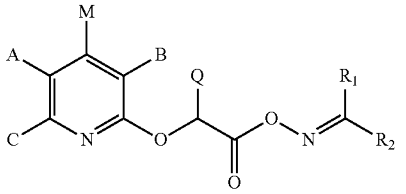

wherein, A, B each independently represent halogen; or alkyl or cycloalkyl with or without halogen;

C represents hydrogen, halogen, alkyl or haloalkyl;

Q represents halogen, cyano, cyanoalkyl, hydroxyalkyl, amino, nitro, formyl; alkyl, alkenyl, alkynyl, cycloalkyl, alkoxy, alkylthio, alkylcarbonyl, alkoxycarbonyl, alkylaminoalkyl or alkoxyalkyl with or without halogen; or unsubstituted or substituted aryl, heteroaryl, arylalkyl or heteroarylalkyl;

$R_1$ and $R_2$ independently represent H, halogen, cyano, nitro, alkyl, haloalkyl, alkenyl, cycloalkyl, alkoxy, acyloxy, alkylthio, unsubstituted or substituted aryl, unsubstituted or substituted benzyl, unsubstituted or substituted heteroaryl, unsubstituted or substituted aryloxy, unsubstituted or substituted arylthio, unsubstituted or substituted heteroaryloxy, unsubstituted or substituted heteroarylthio or the group represented by the formula of —$COR_5$, wherein, $R_5$ represents alkyl, haloalkyl, alkenyl, cycloalkyl, alkoxy, alkenoxy, cycloalkoxy, alkylthio, alkenylthio, cycloalkylthio, unsubstituted or substituted benzyl, unsubstituted or substituted aryl, unsubstituted or substituted heteroaryl, unsubstituted or substituted aryloxy, unsubstituted or substituted heteroaryloxy, unsubstituted or substituted arylalkyloxy, unsubstituted or substituted heteroarylalkyloxy, unsubstituted or substituted arylalkylthio, unsubstituted or substituted heteroarylalkylthio, unsubstituted or substituted benzylthio, unsubstituted or substituted arylthio, unsubstituted or substituted heteroarylthio, or amino which is optionally substituted by alkyl, acyl, acyloxy, unsubstituted or substituted aryl, unsubstituted or substituted heteroaryl, unsubstituted or substituted arylalkyl or unsubstituted or substituted heteroarylalkyl; or $R_1$ and $R_2$ are linked to form a 5- or 6-member saturated or unsaturated ring;

M represents nitro or $NR_3R_4$, wherein $R_3$ represents H; alkyl, alkenyl or alkynyl optionally substituted by 1-2 $R_{11}$; —$COR_{12}$, nitro, $OR_{13}$, $SO_2R_{14}$, $NR_{15}R_{16}$, $N{=}CR_{17}R_{18}$, alkylcarbamoyl, dialkylcarbamoyl, trialkylsilyl or dialkylphosphono; $R_4$ represents H; alkyl optionally substituted by 1-2 $R_{11}$; or —$COR_{12}$; or $NR_3R_4$ represents $N{=}CR_{21}NR_{22}R_{23}$, $N{=}CR_{24}OR_{25}$; or a 5- or 6-membered saturated or unsaturated ring with or without oxygen atom, sulfur atom, or other nitrogen atom, which is unsubstituted or substituted by 1-2 groups independently selected from the group consisting of halogen, alkyl, alkoxy, haloalkoxy, alkylthio, haloalkylthio, amino, alkylamino, dialkylamino and alkoxycarbonyl;

wherein $R_{11}$ independently represents halogen, hydroxy, alkoxy, haloalkoxy, alkylthio, haloalkylthio, amino, alkylamino, dialkylamino, alkoxycarbonyl; or unsubstituted or substituted aryl or heteroaryl;

$R_{12}$ represents H, alkyl, haloalkyl, alkoxy, phenyl, phenoxy or benzyloxy;

$R_{13}$ represents H, alkyl, haloalkyl, phenyl, benzyl or $CHR_{31}C(O)OR_{32}$; $R_{31}$ represents H, alkyl or alkoxy; $R_{32}$ represents H, alkyl or benzyl;

$R_{14}$ represents alkyl or haloalkyl;

$R_{15}$ represents H, alkyl, formyl, alkylacyl, haloalkylacyl, alkoxycarbonyl, phenylcarbonyl, phenoxycarbonyl or benzyloxycarbonyl; $R_{16}$ represents H or alkyl;

$R_{17}$ represents H, alkyl; or phenyl that is unsubstituted or substituted by 1-3 groups selected from the group consisting of halogen, alkyl and alkoxy; $R_{18}$ represents H or alkyl; or $N{=}CR_{17}R_{18}$ represents

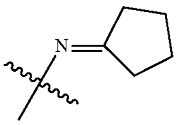 or 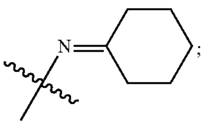;

$R_{21}$, $R_{24}$ each independently represent H or alkyl;

$R_{22}$, $R_{23}$ each independently represent H or alkyl; or $NR_{22}R_{23}$ represents a 5- or 6-membered saturated or unsaturated ring with or without oxygen atom, sulfur atom, or other nitrogen atom;

$R_{25}$ represents alkyl.

Preferably, A, B each independently represent halogen; or C1-C8 alkyl or C3-C8 cycloalkyl with or without halogen;

C represents hydrogen, halogen, C1-C8 alkyl or halo C1-C8 alkyl;

Q represents halogen, cyano, cyano C1-C8 alkyl, hydroxy C1-C8 alkyl, amino, nitro, formyl; C1-C8 alkyl, C2-C8 alkenyl, C2-C8 alkynyl, C3-C8 cycloalkyl, C1-C8 alkoxy, C1-C8 alkylthio, C1-C8 alkylcarbonyl, C1-C8 alkoxycarbonyl, C1-C8 alkylamino C1-C8 alkyl or C1-C8 alkoxy C1-C8 alkyl with or without halogen; or unsubstituted or substituted aryl, heteroaryl, aryl C1-C8 alkyl or heteroaryl C1-C8 alkyl;

$R_1$ and $R_2$ independently represent H, halogen, cyano, nitro, C1-C8 alkyl, halo C1-C8 alkyl, C2-C8 alkenyl, C3-C8 cycloalkyl, C1-C8 alkoxy, C1-C8 acyloxy, C1-C8 alkylthio, unsubstituted or substituted aryl, unsubstituted or substituted benzyl, unsubstituted or substituted heteroaryl, unsubstituted or substituted aryloxy, unsubstituted or substituted arylthio, unsubstituted or substituted heteroaryloxy, unsubstituted or substituted heteroarylthio or the group represented by the formula of —$COR_5$, wherein, $R_5$ represents C1-C8 alkyl, halo C1-C8 alkyl, C2-C8 alkenyl, C3-C8 cycloalkyl, C1-C8 alkoxy, C2-C8 alkenoxy, C3-C8 cycloalkoxy, C1-C8 alkylthio, C2-C8 alkenylthio, C3-C8 cycloalkylthio, unsubstituted or substituted benzyl, unsubstituted or substituted aryl, unsubstituted or substituted heteroaryl, unsubstituted or substituted aryloxy, unsubstituted or substituted heteroaryloxy, unsubstituted or substituted aryl C1-C8 alkyloxy, unsubstituted or substituted heteroaryl C1-C8 alkyloxy, unsubstituted or substituted aryl C1-C8 alkylthio, unsubstituted or substituted heteroaryl C1-C8 alkylthio, unsubstituted or substituted benzylthio, unsubstituted or substituted arylthio, unsubstituted or substituted heteroarylthio, or amino which is optionally substituted by C1-C8 alkyl, C1-C8 acyl, C1-C8 acyloxy, unsubstituted or substituted aryl, unsubstituted or substituted heteroaryl, unsubstituted or substituted aryl C1-C8 alkyl or unsubstituted or substituted heteroaryl C1-C8 alkyl; or $R_1$ and $R_2$ are linked to form a 5- or 6-member saturated carbocyclic ring;

M represents nitro or $NR_3R_4$, wherein $R_3$ represents H; C1-C8 alkyl, C2-C8 alkenyl or C2-C8 alkynyl optionally substituted by 1-2 $R_{11}$; —$COR_{12}$, nitro, $OR_{13}$, $SO_2R_{14}$, $NR_{15}R_{16}$, $N{=}CR_{17}R_{18}$, C1-C8 alkylcarbamoyl, di-C1-C8 alkylcarbamoyl, tri-C1-C8 alkylsilyl or di-C1-C8 alkylphosphono; $R_4$ represents H; C1-C8 alkyl optionally substituted by 1-2 $R_{11}$; or —$COR_{12}$; or $NR_3R_4$ represents $N{=}CR_{21}NR_{22}R_{23}$, $N{=}CR_{24}OR_{25}$; or

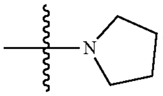,
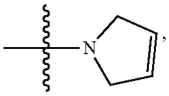,
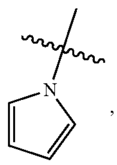,

-continued

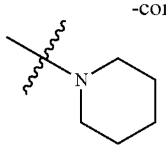
or
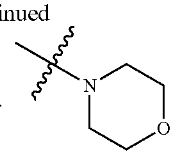

that is unsubstituted or substituted by 1-2 groups independently selected from the group consisting of halogen, C1-C8 alkyl, C1-C8 alkoxy, halo C1-C8 alkoxy, C1-C8 alkylthio, halo C1-C8 alkylthio, amino, C1-C8 alkylamino, di-C1-C8 alkylamino and C1-C8 alkoxycarbonyl;

wherein $R_{11}$ independently represents halogen, hydroxy, C1-C8 alkoxy, halo C1-C8 alkoxy, C1-C8 alkylthio, halo C1-C8 alkylthio, amino, C1-C8 alkylamino, di-C1-C8 alkylamino, C1-C8 alkoxycarbonyl; or phenyl, naphthyl,

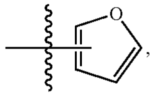,
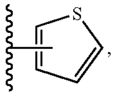,
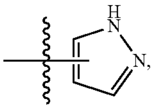,
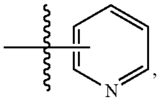,
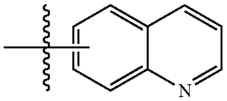
or
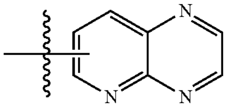

that is unsubstituted or substituted by 1-3 groups selected from the group consisting of halogen, C1-C8 alkyl, halo C1-C8 alkyl, C1-C8 alkoxy and nitro;

$R_{12}$ represents H, C1-C18 alkyl, halo C1-C8 alkyl, C1-C8 alkoxy, phenyl, phenoxy or benzyloxy;

$R_{13}$ represents H, C1-C8 alkyl, halo C1-C8 alkyl, phenyl, benzyl or $CHR_{31}C(O)OR_{32}$; $R_{31}$ represents H, C1-C8 alkyl or C1-C8 alkoxy; $R_{32}$ represents H, C1-C8 alkyl or benzyl;

$R_{14}$ represents C1-C8 alkyl or halo C1-C8 alkyl;

$R_{15}$ represents H, C1-C8 alkyl, formyl, C1-C8 alkylacyl, halo C1-C8 alkylacyl, C1-C8 alkoxycarbonyl, phenylcarbonyl, phenoxycarbonyl or benzyloxycarbonyl; $R_{16}$ represents H or C1-C8 alkyl;

$R_{17}$ represents H, C1-C8 alkyl; or phenyl that is unsubstituted or substituted by 1-3 groups selected from the group consisting of halogen, C1-C8 alkyl and C1-C8 alkoxy; $R_{18}$ represents H or C1-C8 alkyl; or $N{=}CR_{17}R_{18}$ represents

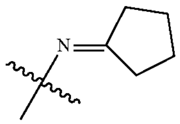
or
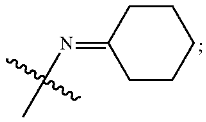;

$R_{21}$, $R_{24}$ each independently represent H or C1-C8 alkyl;

$R_{22}$, $R_{23}$ each independently represent H or C1-C8 alkyl; or $NR_{22}R_{23}$ represents

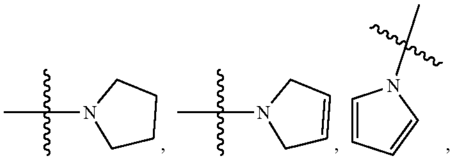

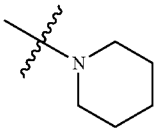 or 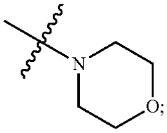

$R_{25}$ represents C1-C8 alkyl;

the term “aryl” refers to phenyl or naphthyl; the term “heteroaryl” refers to an aromatic ring group containing 3 to 6 ring atoms and is optionally fused via benzo ring, 1 to 4 heteroatoms in the ring atoms being selected from oxygen, nitrogen and sulfur, for example,

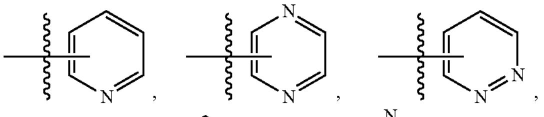

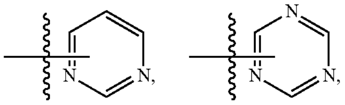

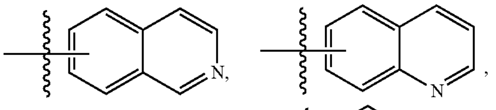

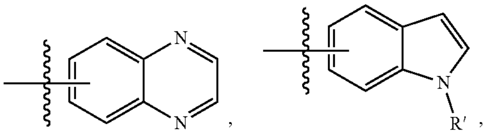

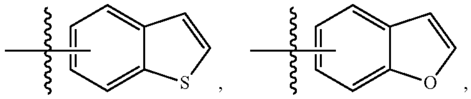

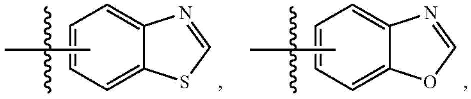

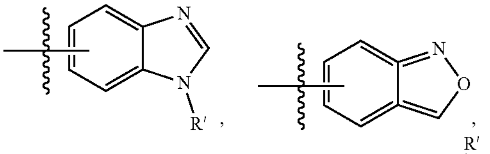

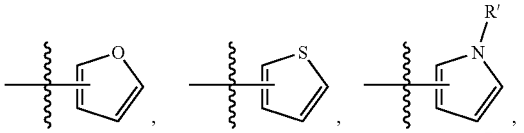

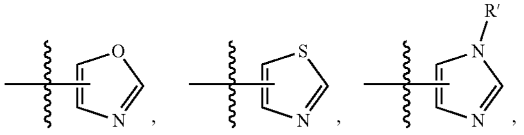

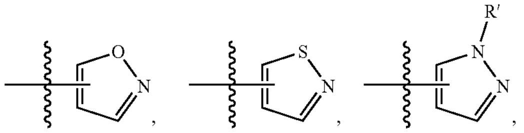

-continued

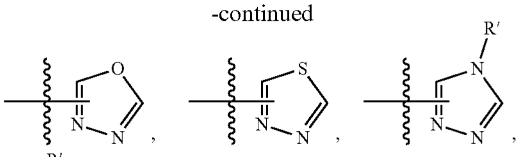

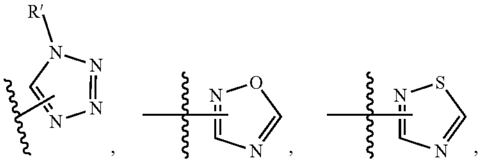

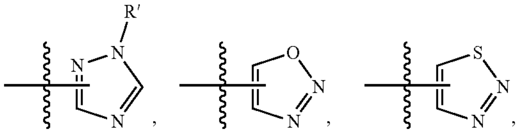

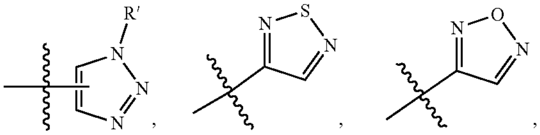

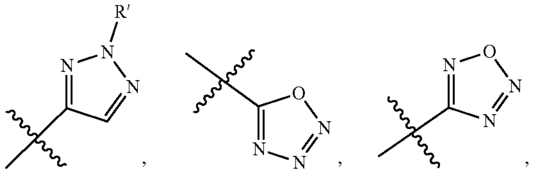

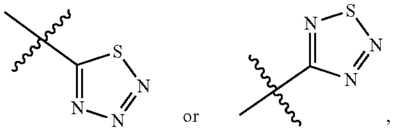

which is optionally substituted by at least one group selected from the group consisting of halogen, nitro, cyano, thiocyano, hydroxy, carboxy, mercapto, formyl; phenyl, benzyl, benzyloxy or phenoxy that is unsubstituted or substituted by at least one group from the group consisting of halogen, alkyl and alkoxy; alkyl, alkenyl, alkynyl, cycloalkyl, cycloalkylalkyl, OR", SR", -alkyl-OR", -alkyl-SR", COR", COOR", COSR", SOR", $SO_2R$", OCOR" or SCOR" with or without halogen; and amino or aminocarbonyl substituted by one or two groups selected from the group consisting of hydrogen, alkyl, alkenyl, alkynyl, cycloalkyl, cycloalkylalkyl, phenyl, benzyl, benzyloxy, phenoxy, COR", COOR", $SO_2R$" and OR";

R' each independently represents hydrogen, nitro, hydroxy, amino; or alkyl, alkenyl, alkynyl, cycloalkyl, cycloalkenyl, cycloalkylalkyl, alkoxy, alkenyloxy, alkynyloxy, cycloalkyloxy, alkoxyalkyl, alkoxycarbonyl, alkylthiocarbonyl, alkylsulfonyl, alkylsulfonylalkyl, alkylcarbonyl, alkylcarbonylalkyl, alkylacyloxy, alkylamino, alkylaminocarbonyl, alkoxyaminocarbonyl, alkoxycarbonylalkyl, alkylaminocarbonylalkyl, trialkylsilyl or dialkylphosphono with or without halogen;

R" each independently represents hydrogen, alkyl, alkenyl, alkynyl, cycloalkyl or cycloalkylalkyl.

More preferably, A, B each independently represent halogen; or C1-C6 alkyl or C3-C6 cycloalkyl with or without halogen;

C represents hydrogen, halogen, C1-C6 alkyl or halo C1-C6 alkyl;

Q represents halogen, cyano, cyano C1-C6 alkyl, hydroxy C1-C6 alkyl, amino, nitro, formyl; C1-C6 alkyl, C2-C6 alkenyl, C2-C6 alkynyl, C3-C6 cycloalkyl, C1-C6 alkoxy, C1-C6 alkylthio, C1-C6 alkylcarbonyl, C1-C6 alkoxycarbonyl, C1-C6 alkylamino C1-C6 alkyl or C1-C6 alkoxy C1-C6 alkyl with or without halogen; or unsubstituted or substituted aryl, heteroaryl, aryl C1-C6 alkyl or heteroaryl C1-C6 alkyl;

$R_1$ and $R_2$ independently represent H, cyano, C1-C6 alkyl, halo C1-C6 alkyl, C2-C6 alkenyl, C3-C6 cycloalkyl, C1-C6 alkoxy, C1-C6 acyloxy, C1-C6 alkylthio, unsubstituted or substituted aryl, unsubstituted or substituted benzyl, unsubstituted or substituted heteroaryl, unsubstituted or substituted aryloxy, unsubstituted or substituted arylthio, unsubstituted or substituted heteroaryloxy, unsubstituted or substituted heteroarylthio or the group represented by the formula of —$COR_5$, wherein, $R_5$ represents C1-C6 alkyl, halo C1-C6 alkyl, C2-C6 alkenyl, C3-C6 cycloalkyl, C1-C6 alkoxy, C2-C6 alkenoxy, C3-C6 cycloalkoxy, C1-C6 alkylthio, C2-C6 alkenylthio, C3-C6 cycloalkylthio, unsubstituted or substituted benzyl, unsubstituted or substituted aryl, unsubstituted or substituted heteroaryl, unsubstituted or substituted aryloxy, unsubstituted or substituted heteroaryloxy, unsubstituted or substituted aryl C1-C6 alkyloxy, unsubstituted or substituted heteroaryl C1-C6 alkyloxy, unsubstituted or substituted aryl C1-C6 alkylthio, unsubstituted or substituted heteroaryl C1-C6 alkylthio, unsubstituted or substituted benzylthio, unsubstituted or substituted arylthio, unsubstituted or substituted heteroarylthio, or amino which is optionally substituted by C1-C6 alkyl, C1-C6 acyl, C1-C6 acyloxy, unsubstituted or substituted aryl, unsubstituted or substituted heteroaryl, unsubstituted or substituted aryl C1-C6 alkyl or unsubstituted or substituted heteroaryl C1-C6 alkyl; or $R_1$ and $R_2$ are linked to form a 5- or 6-member saturated carbocyclic ring;

M represents nitro or $NR_3R_4$, wherein $R_3$ represents H; C1-C6 alkyl, C2-C6 alkenyl or C2-C6 alkynyl optionally substituted by 1-2 $R_{11}$; —$COR_{12}$, nitro, $OR_{13}$, $SO_2R_{14}$, $NR_{15}R_{16}$, $N{=}CR_{17}R_{18}$, C1-C6 alkylcarbamoyl, di-C1-C6 alkylcarbamoyl, tri-C1-C6 alkylsilyl or di-C1-C6 alkylphosphono; $R_4$ represents H; C1-C6 alkyl optionally substituted by 1-2 $R_{11}$; or —$COR_{12}$; or $NR_3R_4$ represents $N{=}CR_{21}NR_{22}R_{23}$, $N{=}CR_{24}OR_{25}$; or

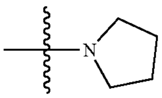, 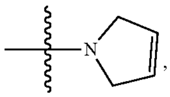, 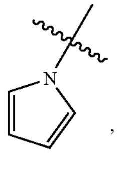,

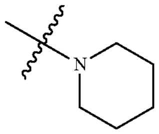 or 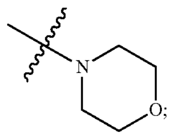;

that is unsubstituted or substituted by 1-2 groups independently selected from the group consisting of halogen, C1-C6 alkyl, C1-C6 alkoxy, halo C1-C6 alkoxy, C1-C6 alkylthio, halo C1-C6 alkylthio, amino, C1-C6 alkylamino, di-C1-C6 alkylamino and C1-C6 alkoxycarbonyl;

wherein $R_{11}$ independently represents halogen, hydroxy, C1-C6 alkoxy, halo C1-C6 alkoxy, C1-C6 alkylthio, halo C1-C6 alkylthio, amino, C1-C6 alkylamino, di-C1-C6 alkylamino, C1-C6 alkoxycarbonyl; or phenyl, naphthyl,

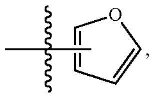, 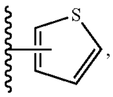, 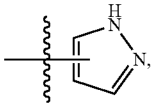,

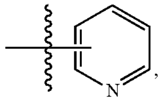, 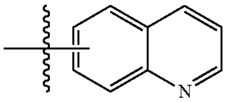 or

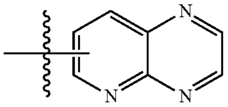

that is unsubstituted or substituted by 1-3 groups selected from the group consisting of halogen, C1-C6 alkyl, halo C1-C6 alkyl, C1-C6 alkoxy and nitro;

$R_{12}$ represents H, C1-C14 alkyl, halo C1-C6 alkyl, C1-C6 alkoxy, phenyl, phenoxy or benzyloxy;

$R_{13}$ represents H, C1-C6 alkyl, halo C1-C6 alkyl, phenyl, benzyl or $CHR_{31}C(O)OR_{32}$; $R_{31}$ represents H, C1-C6 alkyl or C1-C6 alkoxy; $R_{32}$ represents H, C1-C6 alkyl or benzyl;

$R_{14}$ represents C1-C6 alkyl or halo C1-C6 alkyl;

$R_{15}$ represents H, C1-C6 alkyl, formyl, C1-C6 alkylacyl, halo C1-C6 alkylacyl, C1-C6 alkoxycarbonyl, phenylcarbonyl, phenoxycarbonyl or benzyloxycarbonyl; $R_{16}$ represents H or C1-C6 alkyl;

$R_{17}$ represents H, C1-C6 alkyl; or phenyl that is unsubstituted or substituted by 1-3 groups selected from the group consisting of halogen, C1-C6 alkyl and C1-C6 alkoxy; $R_{18}$ represents H or C1-C6 alkyl; or $N{=}CR_{17}R_{18}$ represents

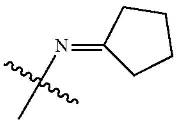 or 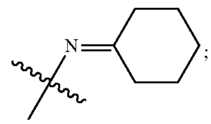;

$R_{21}$, $R_{24}$ each independently represent H or C1-C6 alkyl;

$R_{22}$, $R_{23}$ each independently represent H or C1-C6 alkyl; or $NR_{22}R_{23}$ represents

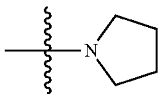, 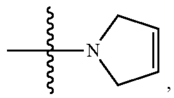,

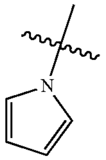, 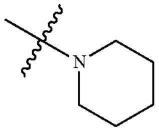 or

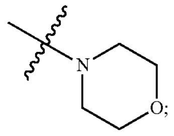;

$R_{25}$ represents C1-C6 alkyl;

the term "aryl" refers to phenyl or naphthyl; the term "heteroaryl" refers to

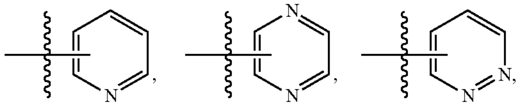

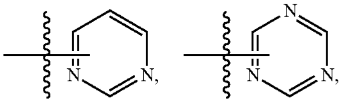

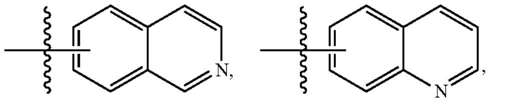

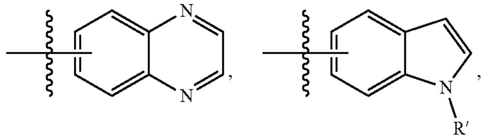

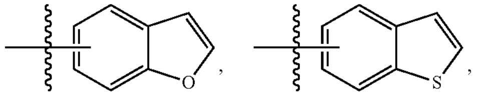

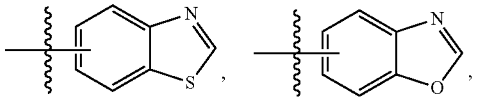

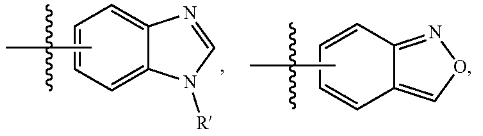

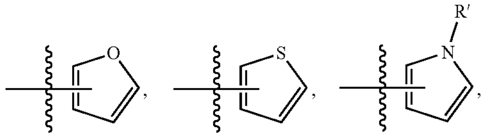

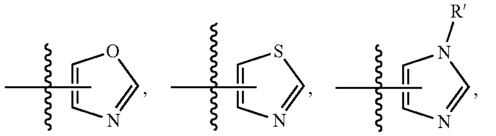

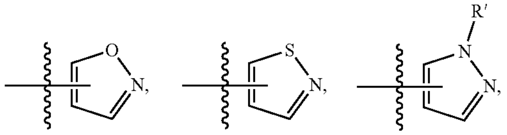

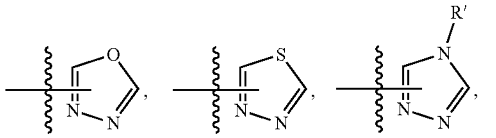

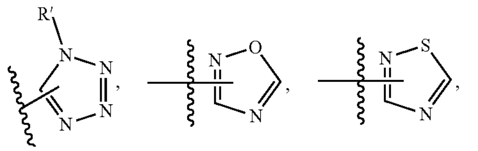

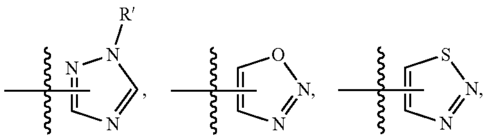

-continued

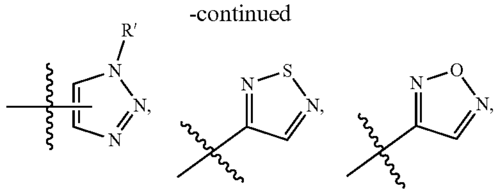

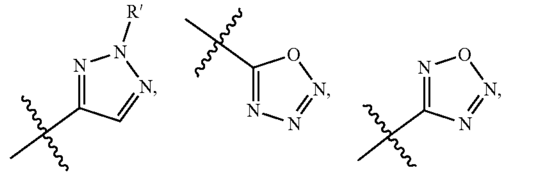

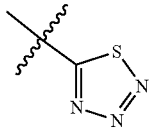

or

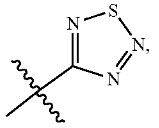

which is substituted by 0, 1, 2 or 3 groups selected from the group consisting of halogen, nitro, cyano, thiocyano, hydroxy, carboxy, mercapto, formyl; phenyl, benzyl, benzyloxy or phenoxy that is unsubstituted or substituted by at least one group from the group consisting of halogen, C1-C6 alkyl and C1-C6 alkoxy; C1-C6 alkyl, C2-C6 alkenyl, C2-C6 alkynyl, C3-C6 cycloalkyl, C3-C6 cycloalkyl C1-C6 alkyl, OR", SR", —(C1-C6)alkyl-OR", —(C1-C6)alkyl-SR", COR", COOR", COSR", SOR", $SO_2R$", OCOR" or SCOR" with or without halogen; and amino or aminocarbonyl substituted by one or two groups selected from the group consisting of hydrogen, C1-C6 alkyl, C2-C6 alkenyl, C2-C6 alkynyl, C3-C6 cycloalkyl, C3-C6 cycloalkyl C1-C6 alkyl, phenyl, benzyl, benzyloxy, phenoxy, COR", COOR", $SO_2R$" and OR";

R' each independently represents hydrogen, nitro, hydroxy, amino; or C1-C6 alkyl, C2-C6 alkenyl, C2-C6 alkynyl, C3-C6 cycloalkyl, C3-C6 cyclo alkenyl, C3-C6 cycloalkyl C1-C6 alkyl, C1-C6 alkoxy, C2-C6 alkenyloxy, C2-C6 alkynyloxy, C3-C6 cycloalkyloxy, C1-C6 alkoxy C1-C6 alkyl, C1-C6 alkoxycarbonyl, C1-C6 alkylthiocarbonyl, C1-C6 alkylsulfonyl, C1-C6 alkylsulfonyl C1-C6 alkyl, C1-C6 alkylcarbonyl, C1-C6 alkylcarbonyl C1-C6 alkyl, C1-C6 alkylacyloxy, C1-C6 alkylamino, C1-C6 alkylaminocarbonyl, C1-C6 alkoxyaminocarbonyl, C1-C6 alkoxycarbonyl C1-C6 alkyl, C1-C6 alkylaminocarbonyl C1-C6 alkyl, tri-C1-C6 alkylsilyl, di-C1-C6 alkylphosphono with or without fluoro, chloro or bromo;

R" each independently represents hydrogen, C1-C6 alkyl, C2-C6 alkenyl, C2-C6 alkynyl, C3-C6 cycloalkyl or C3-C6 cycloalkyl C1-C6 alkyl.

Further preferably, A, B each independently represent halogen, C1-C6 alkyl, halo C1-C6 alkyl or C3-C6 cycloalkyl;

C represents hydrogen, halogen, C1-C6 alkyl or halo C1-C6 alkyl;

Q represents C1-C6 alkyl, halo C1-C6 alkyl, C3-C6 cycloalkyl, C2-C6 alkenyl, C2-C6 alkynyl, halogen, cyano, amino, nitro, formyl, C1-C6 alkoxy, C1-C6 alkylthio, C1-C6 alkoxycarbonyl, hydroxy C1-C6 alkyl, C1-C6 alkoxy C1-C2 alkyl, cyano C1-C2 alkyl, C1-C6 alkylamino C1-C2 alkyl, benzyl, naphthyl, furyl, thienyl, thiazolyl, pyridyl, pyrimidinyl;

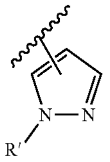

that is unsubstituted or substituted by C1-C6 alkyl; or phenyl that is unsubstituted or substituted by at least one group selected from the group consisting of C1-C6 alkyl, halo C1-C6 alkyl, halogen and C1-C6 alkoxy;

R' represents C1-C6 alkyl or halo C1-C6 alkyl.

$R_1$ and $R_2$ independently represent H, halogen, C1-C6 alkyl, halo C1-C6 alkyl, C3-C6 cycloalkyl, C2-C6 alkenyl, C1-C6 alkoxy, C1-C6 alkylthio, cyano, nitro, benzyl, phenoxy, phenylthio, naphthyl; phenyl that is unsubstituted or substituted by one or more group selected from the group consisting of halogen, C1-C6 alkyl, halo C1-C6 alkyl, C3-C6 cycloalkyl, nitro, cyano, C1-C6 alkoxy, C1-C6 alkylthio, C2-C6 alkenyloxy, amino, C1-C6 alkylamino, C1-C6 alkylcarbonylamino, C1-C6 alkylphenylamino and phenoxyamino; or the group represented by the formula of —$COR_5$, wherein, $R_5$ represents C1-C6 alkyl, C1-C6 alkoxy, C1-C6 alkylthio, C2-C6 alkenoxy, phenoxy, benzyloxy, pyrrolyl C1-C2 alkyloxy, C1-C6 alkylamino, C1-C6 alkylamino, C1-C6 alkylphenylamino, furyl C1-C2 alkylamino, phenylethyleneamino; or benzylamino that is unsubstituted or substituted by C1-C6 alkyl, halogen or C1-C6 alkoxy;

Or

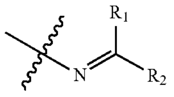

represents

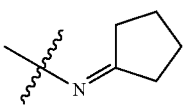 or 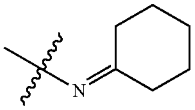 ;

M represents amino, C1-C6 alkylamino, C1-C6 alkylcarbonylamino, phenylcarbonylamino, benzylamino; or furylmethyleneamino that is unsubstituted or substituted by halo C1-C6 alkyl.

More further preferably, A, B each independently represent fluoro, chloro, bromo, iodo, methyl, ethyl, propyl, isopropyl, trifluoromethyl or cyclopropyl;

C represents hydrogen, fluoro, chloro, bromo, iodo, methyl or trifluoromethyl;

Q represents methyl, ethyl, propyl, isopropyl, cyclopropyl, vinyl, ethynyl, fluoro, chloro, bromo, cyano, amino, nitro, formyl, methoxy, methylthio, methoxycarbonyl, monochloromethyl, monofluoromethyl, difluoromethyl, trifluoromethyl, 2-chloroethyl, 2,2,2-trifluoroethyl, hydroxymethyl,

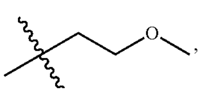, 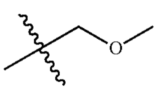, 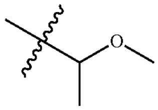,

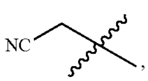, 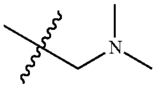, benzyl, naphthyl, furyl, thienyl, thiazolyl, pyridyl, pyrimidinyl;

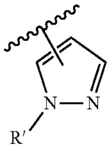, that is unsubstituted or substituted by methyl; or phenyl that is unsubstituted or substituted by at least one group selected from the group consisting of methyl, trifluoromethyl, chloro and methoxy;

R' represents methyl, ethyl or difluoromethyl;

$R_1$ and $R_2$ independently represent hydrogen, fluorine, chlorine, bromine, methyl, ethyl, propyl, isopropyl, n-butyl, tert-butyl, cyclopropyl, allyl, 2-chloroethyl, methylthio, ethylthio, ethoxy, cyano, nitro, benzyl, phenoxy, phenylthio, naphthyl; phenyl that is unsubstituted or substituted by one or more group selected from the group consisting of fluoro, chloro, ethyl, cyclopropyl, trifluoromethyl, nitro, cyano, methoxy, methylthio, propenyloxy, amino, dimethylamino, acetamido, phenoxyamino and methylphenylamino; or the group represented by the formula of —$COR_5$, wherein, $R_5$ represents methyl, ethyl, methoxy, ethoxy, methylthio, vinyloxy, phenoxy, benzyloxy, pyrrolylmethyleneoxy, dimethylamino, propylamino, methylphenylamino, furylmethyleneamino, phenethylenylamino, or benzylamino that is unsubstituted or substituted by methyl, chloro or methoxy;

Or

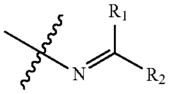

represents

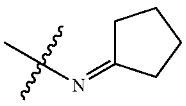 or 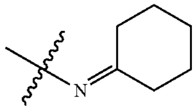 ;

M represents $NH_2$,

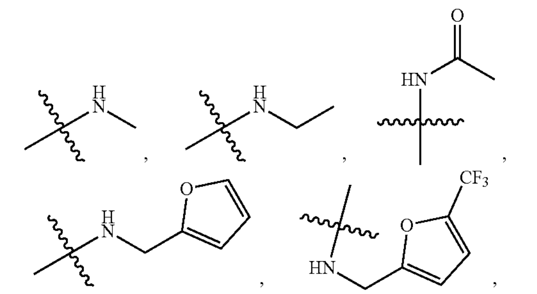

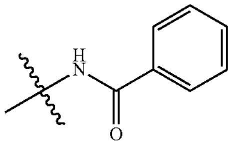

or

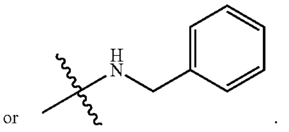

In the definition of the compound represented by the above general formula I and in all the structural formula below, the term, whether used alone or in a compound name, refers to the following substituent: an alkyl group having more than two carbon atoms may be straight or branched. For example, in the compound name "-alkyl-OR'''", alkyl may be $—CH_2—$, $—CH_2CH_2—$, $—CH(CH_3)—$, $—C(CH_3)_2—$ and the like. The alkyl group is, for example, C1 alkyl-methyl; C2 alkyl-ethyl; C3 alkyl-propyl such as n-propyl or isopropyl; C4 alkyl-butyl such as n-butyl, isobutyl, tert-butyl or 2-butyl; C5 alkyl-pentyl such as n-pentyl; C6-alkyl-hexyl such as n-hexyl, isohexyl or 1,3-dimethylbutyl. Similarly, alkenyl includes, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl includes, for example, propargyl, but-2-yn-1-yl, but-3-yn-1-yl, 1-methylbut-3-yn-1-yl. Multiple bond can be at any position of each unsaturated group. Cycloalkyl is a carbocyclic saturated ring system having, for example, three to six carbon atoms, such as cyclopropyl, cyclobutyl, cyclopentyl or cyclohexyl. Similarly, cycloalkenyl is a monocyclic alkenyl having, for example, three to six carbocyclic members, such as cyclopropenyl, cyclobutenyl, cyclopentenyl, and cyclohexenyl, wherein double bond can be at any position. Halogen is fluorine, chlorine, bromine or iodine If a group is substituted by a group, it is understood to mean that the group is substituted by one or more identical or different groups selected from those mentioned above. Further, the same or different substitution characters contained in the same or different substituents are independently selected, and may be the same or different.

In addition, unless specifically indicated, the term occurring before or after multiple juxtaposed substituents (separated by "," or "or") in the present invention has a limiting effect on each of the subsequent substituents, for example, the term "with or without halogen" in "alkyl or cycloalkylalkyl with or without halogen" has a limiting effect on each of the following groups "alkyl" and "cycloalkylalkyl"; a group (including heterocyclyl, aryl, etc.) without being specified a linking site may be attached at any site, including a C or N site; if it is substituted, the substituent may be substituted at any site as long as it comply with the valence bond theory. For example, if the heteroaryl

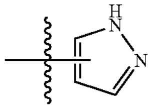

is substituted with one methyl, it can be

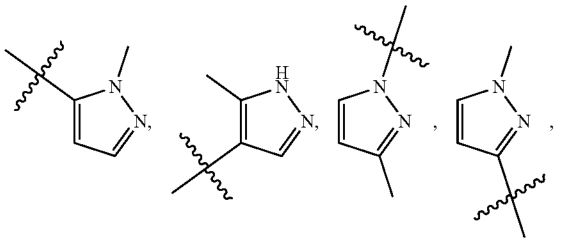

etc.

Depending on the property of substituents and the linkage manner thereof, the compound of Formula I may exist as a stereoisomer. For example, if a compound has one or more asymmetric carbon atoms, it may has enantiomers and diastereomers. The stereoisomer can be obtained from the mixtures obtained in the preparation by conventional separation methods, for example by chromatographic separation. The stereoisomer may also be prepared selectively by using stereoselective reactions and using optically active starting materials and/or auxiliaries. The present invention also relates to all stereoisomers and mixtures thereof which are included in the general Formula I but are not specifically defined.

The preparation method of the pyridyloxy carboxylic oxime derivative comprises the following steps:

A compound of formula II is reacted with a compound of formula III to obtain a compound of formula I; the reaction scheme is as follows:

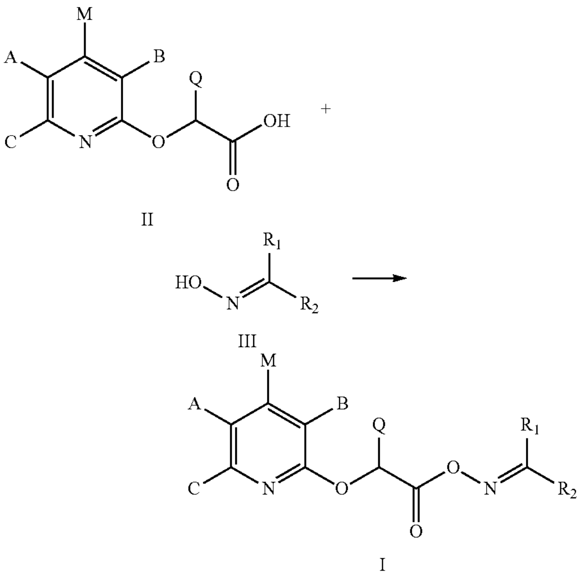

II III I wherein, the reaction is carried out in the presence of a dehydrant and a solvent, preferably the dehydrant is DCC, and the solvent is one or more selected from the group consisting of dichloromethane, dichloroethane, acetonitrile, N,N-dimethylformamide, N,N-dimethylacetamide, dimethyl sulfoxide, tetrahydrofuran, toluene and xylene.

A herbicidal composition comprising (i) at least one of the pyridyloxy carboxylic oxime derivatives of the formula I; preferably, further comprising (ii) one or more further herbicides and/or safeners; more preferably, further comprising (iii) agrochemically acceptable formulation auxiliaries.

A method for controlling a weed comprising applying a herbicidally effective amount of at least one of the pyridyloxy carboxylic oxime derivatives or the herbicidal composition on a plant or in a weed area. Preferably, the plant is rice (such as *japonica* rice, *indica* rice); or the weed is a gramineous weed (such as *Digitaria sanguinalis, Echinochloa crusgalli, Setaria viridis, Leptochloa chinensis*), a broad-leaved weed (such as *Monochoria Vaginalis, Galium spurium, Sagittaria trifolia, Murdannia triquetra*) or cyperaceae weed (such as *Cyperus* iria, *Scirpus* juncoides).

Use of at least one of the pyridyloxy carboxylic oxime derivatives or the herbicidal composition for controlling a weed, preferably, the pyridyloxy carboxylic oxime derivatives thereof being used to control a weed in a useful crop, wherein the useful crop is a genetically modified crop or a crop treated by gene editing technology. Preferably, the crop is rice (such as *japonica* rice, *indica* rice); or the weed is a gramineous weed (such as *Digitaria sanguinalis, Echinochloa crusgalli, Setaria viridis, Leptochloa chinensis*), a broad-leaved weed (such as *Monochoria Vaginalis, Galium spurium, Sagittaria trifolia, Murdannia triquetra*) or cyperaceae weed (such as *Cyperus* iria, *Scirpus* juncoides).

The compounds of the formula I according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and Sorghum, and also perennial *Cyperus* species.

In the case of the dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from amongst the annuals, and *Convolvulus, Cirsium, Rumex* and *Artemisia* in the case of the perennial weeds. The active compounds according to the invention also effect outstanding control of harmful plants which occur under the specific conditions of rice growing such as, for example, *Echinochloa, Sagittaria, Alisma, Eleocharis, Scirpus* and *Cyperus*. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against *Apera spica venti, Chenopodium album, Lamium purpureum, Polygonum convulvulus, Stellaria media, Veronica hederifolia, Veronica persica, Viola tricolor* and against *Amaranthus, Galium* and *Kochia* species.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. In particular, they have excellent compatibility in cereals, such as wheat, barley and corn, in particular wheat. For these reasons, the present compounds are highly suitable for selectively controlling undesired plant growth in plantings for agricultural use or in plantings of ornamentals.

Owing to their herbicidal properties, these active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of the formula I according to the invention or their salts in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compounds of the formula I can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of genetically engineered changes in crop plants in order to modify the starch synthesized in the plants (for example WO 92/11376, WO 92/14827, WO 91/19806), transgenic crop plants which are resistant to certain herbicides of the glufosinate (Glufosinate ammonium)-(cf., for example, EP-A 0 242 236, EP-A 0 242 246) or glyphosate-type (WO 92/00377), or of the sulfonylurea-type (EP-A 0 257 993, U.S. Pat. No. 5,013,659 A), transgenic crop plants, for example cotton, having the ability to produce *Bacillus thuringiensis* toxins (Bt toxins) which impart resistance to certain pests to the plants (EP-A 0 142 924, EP-A 0 193 259), transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N. Y.; or Winnacker "Gene und Klone" [Genes and Clones], VCH Weinheim, 2nd edition 1996, or Christou, "Trends in Plant Science" 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i. e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling harmful plants in transgenic crop plants.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising compounds of the formula I. The compounds of the formula I can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil dispersions (OD), oil- or water-based dispersions, oil-miscible solutions, dusts (DP), capsule suspensions (CS), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Technology], Volume 7, C. Hauser Verlag Munich, 4th. Edition 1986; Wade van Valkenburg, "Pesticide Formulations", Marcel Dekker, N. Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N. J., H. v. Olphen, "Introduction to Clay Colloid Chemistry"; 2nd Ed., J. Wiley & Sons, N. Y.; C. Marsden, "Solvents Guide"; 2nd Ed., Interscience, N. Y. 1963; McCutcheon's "Detergents and Emulsifiers Annual", MC Publ. Corp., Ridgewood N. J.; Sisley and Wood, "Encyclopedia of Surface Active Agents", Chem. Publ. Co. Inc., N. Y. 1964; Schönfeldt, "Grenzflüchenaktive Äthylenoxidaddkte" [Surface-active ethylene oxide adducts], Wiss. Verlagagesell. Stuttgart 1976; Winnacker-Küchler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyinaphthalenesulfona-te or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57. For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally contain from 0.1 to 99% by weight, in particular from 0.1 to 95% by weight, of active compound of the formula I. In wettable powders the concentration of active compound is, for example, from about 10 to 99% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Suitable active compounds which can be combined with the active compounds according to the invention in mixed formulations or in a tank mix are, for example, known active compounds as described in for example World Herbicide New Product Technology Handbook, China Agricultural Science and Farming Techniques Press, 2010. 9 and in the literature cited therein. For example the following active compounds may be mentioned as herbicides which can be combined with the compounds of the formula I (note: the compounds are either named by the "common name" in accordance with the International Organization for Standardization (ISO) or by the chemical names, if appropriate together with a customary code number): acetochlor, butachlor, alachlor, propisochlor, metolachlor, s-metolachlor, pretilachlor, propachlor, ethachlor, napropamide, R-left handed napropamide, propanil, mefenacet, diphenamid, diflufenican, ethaprochlor, beflubutamid, bromobutide, dimethenamid, dimethenamid-P, etobenzanid, flufenacet, thenylchlor, metazachlor, isoxaben, flamprop-M-methyl, flamprop-M-propyl, allidochlor, pethoxamid, chloranocryl, cyprazine, mefluidide, monalide, delachlor, prynachlor, terbuchlor, xylachlor, dimethachlor, cisanilide, trimexachlor, clomeprop, propyzamide, pentanochlor, carbetamide, benzoylprop-ethyl, cyprazole, butenachlor, tebutam, benzipram, mogrton, dichlofluanid, naproanilide, diethatyl-ethyl, naptalam, flufenacet, benzadox, chlorthiamid, chlorophthalimide, isocarbamide, picolinafen, atrazine, simazine, prometryn, cyanatryn, simetryn, ametryn, propazine, dipropetryn, SSH-108, terbutryn, terbuthylazine, triaziflam, cyprazine, proglinazine, trietazine, prometon, simetone, aziprotryne, desmetryn, dimethametryn, procyazine, mesoprazine, sebuthylazine, secbumeton, terbumeton, methoprotryne, cyanatryn, ipazine, chlorazine, atraton, pendimethalin, eglinazine, cyanuric acid, indaziflam, chlorsulfuron, metsulfuron-methyl, bensulfuron methyl, chlorimuron-ethyl, tribenuron-methyl, thifensulfuron-methyl, pyrazosulfuron-ethyl, mesosulfuron, iodosulfuron-methyl sodium, foramsulfuron, cinosulfuron, triasulfuron, sulfometuron methyl, nicosulfuron, ethametsulfuron-methyl, amidosulfuron, ethoxysulfuron, cyclosulfamuron, rimsulfuron, azimsulfuron, flazasulfuron, monosulfuron, monosulfuron-ester, flucarbazone-sodium, flupyrsulfuron-methyl, halosulfuron-methyl, oxasulfuron, imazosulfuron, primisulfuron, propoxycarbazone, prosulfuron, sulfosulfuron, trifloxysulfuron, triflusulfuron-methyl, tritosulfuron, sodium metsulfuron methyl, flucetosulfuron, HNPC-C, orthosulfamuron, propyrisulfuron, metazosulfuron, acifluorfen, fomesafen, lactofen, fluoroglycofen, oxyfluorfen, chlornitrofen, aclonifen, ethoxyfen-ethyl, bifenox, nitrofluorfen, chlomethoxyfen, fluorodifen, fluoronitrofen, furyloxyfen, nitrofen, TOPE, DMNP, PPG1013, AKH-7088, halosafen, chlortoluron, isoproturon, linuron, diuron, dymron, fluometuron, benzthiazuron, methabenzthiazuron, cumyluron, ethidimuron, isouron, tebuthiuron, buturon, chlorbromuron, methyldymron, phenobenzuron, SK-85, metobromuron, metoxuron, afesin, monuron, siduron, fenuron, fluothiuron, neburon, chloroxuron, noruron, isonoruron, 3-cyclooctyl-1, thiazfluron, tebuthiuron, difenoxuron, parafluron, methylamine tribunil, karbutilate, trimeturon, dimefuron, monisouron, anisuron, methiuron, chloreturon, tetrafluron, phenmedipham, phenmedipham-ethyl, desmedipham, asulam, terbucarb, barban, propham, chlorpropham, rowmate, swep, chlorbufam, carboxazole, chlorprocarb, fenasulam, BCPC, CPPC, carbasulam, butylate, benthiocarb, vernolate, molinate, triallate, dimepiperate, esprocarb, pyributicarb, cycloate, avadex, EPTC, ethiolate, orbencarb, pebulate, prosulfocarb, tiocarbazil, CDEC, dimexano, isopolinate, methiobencarb, 2,4-D butyl ester, MCPA-Na, 2,4-D isooctyl ester, MCPA isooctyl ester, 2,4-D sodium salt, 2,4-D dimethyla mine salt, MCPA-thioethyl, MCPA, 2,4-D propionic acid, high 2,4-D propionic acid salt, 2,4-D butyric acid, MCPA propionic acid, MCPA propionic acid salt, MCPA butyric acid, 2,4,5-D, 2,4,5-D propionic acid, 2,4,5-D butyric acid, MCPA amine salt, dicamba, erbon, chlorfenac, saison, TBA, chloramben, methoxy-TBA, diclofop-methyl, fluazifop-butyl, fluazifop-p-butyl, haloxyfop-methyl, haloxyfop-P, quizalofop-ethyl, quizalofop-p-ethyl, fenoxaprop-ethy, fenoxaprop-p-ethyl, propaquizafop, cyhalofop-butyl, metamifop, clodinafop-propargyl, fenthiaprop-ethyl, chloroazifop-propynyl, poppenate-methyl, trifopsime, isoxapyrifop, paraquat, diquat, oryzalin, ethalfluralin, isopropalin, nitralin, profluralin, prodinamine, benfluralin, fluchloraline, dinitramina, dipropalin, chlornidine, methalpropalin, dinoprop, glyphosate, anilofos, glufosinate ammonium, amiprophos-methyl, sulphosate, piperophos, bialaphos-sodium, bensulide, butamifos, phocarb, 2,4-DEP, H-9201, zytron, imazapyr, imazethapyr, imazaquin, imazamox, imazamox ammonium salt, imazapic, imazamethabenz-methyl, fluroxypyr, fluroxypyr isooctyl ester, clopyralid, picloram, trichlopyr, dithiopyr, haloxydine, 3,5,6-trichloro-2-pyridinol, thiazopyr, fluridone, aminopyralid, diflufenzopyr, triclopyr-butotyl, Cliodinate, sethoxydim, clethodim, cycloxydim, alloxydim, clefoxydim, butroxydim, tralkoxydim, tepraloxydim, buthidazole, metribuzin, hexazinone, metamitron, ethiozin, ametridione, amibuzin, bromoxynil, bromoxynil octanoate, ioxynil octanoate, ioxynil, dichlobenil, diphenatrile, pyraclonil, chloroxynil, iodobonil, flumetsulam, florasulam, penoxsulam, metosulam, cloransulam-methyl, diclosulam, pyroxsulam, benfuresate, bispyribac-sodium, pyribenzoxim, pyriftalid, pyriminobac-methyl, pyrithiobac-sodium, benzobicylon, mesotrione, sulcotrione, tembotrione, tefuryltrione, bicyclopyrone, ketodpiradox, isoxaflutole, clomazone, fenoxasulfone, methiozolin, fluazolate, pyraflufen-ethyl, pyrazolynate, difenzoquat, pyrazoxyfen, benzofenap, nipyraclofen, pyrasulfotole, topramezone, pyroxasulfone, cafenstrole, flupoxam, aminotriazole, amicarbazone, azafenidin, carfentrazone-ethyl, sulfentrazone, bencarbazone, benzfendizone, butafenacil, bromacil, isocil, lenacil, terbacil, flupropacil, cinidon-ethyl, flumiclorac-pentyl, flumioxazin, propyzamide, MK-129, flumezin, pentachlorophenol, dinoseb, dinoterb, dinoterb acetate, dinosam, DNOC, chloronitrophene, medinoterb acetate, dinofenate, oxadiargyl, oxadiazon, pentoxazone, Flufenacet, fluthiacet-methyl, fentrazamide, flufenpyr-ethyl, pyrazon, brompyrazon, metflurazon, kusakira, dimidazon, oxapyrazon, norflurazon, pyridafol, quinclorac, quinmerac, bentazone, pyridate, oxaziclomefone, benazolin, clomazone, cinmethylin, ZJ0702, pyribambenz-propyl, indanofan, sodium chlorate, dalapon, trichloroacetic acid, monochloroacetic acid, hexachloroacetone, flupropanate, cyperquat, bromofenoxim, epronaz, methazole, flurtamone, benfuresate, ethofumesate, tioclorim, chlorthal, fluorochloridone, tavron, acrolein, bentranil, tridiphane, chlorfenpropmethyl, thidiarizonaimin, phenisopham, busoxinone, methoxyphenone, saflufenacil, clacyfos, chloropon, alorac, diethamquat, etnipromid, iprymidam, ipfencarbazone, thiencarbazone-methyl, pyrimisulfan, chlorflurazole, tripropindan, sulglycapin, prosulfalin, cambendichlor, aminocyclopyrachlor, rodethanil, benoxacor, fenclorim, flurazole, fenchlorazole-ethyl, cloquintocet-mexyl, oxabetrinil, MG/91, cyometrinil, DKA-24, mefenpyr-diethyl, furilazole, fluxofenim, isoxadifen-ethyl, dichlormid, halauxifen-methyl, DOW florpyrauxifen, UBH-509, D489, LS 82-556, KPP-300, NC-324, NC-330, KH-218, DPX-N8189, SC-0744, DOWCO535, DK-8910, V-53482, PP-600, MBH-001, KIH-9201, ET-751, KIH-6127 and KIH-2023.

In the context of the present specification, if an abbreviation of a generic name of an active compound is used, it includes in each case all customary derivatives, such as esters and salts, as well as isomers, in particular optical isomers, especially one or more commercially available forms. If the generic name denotes an ester or a salt, it also includes in each case all other conventional derivatives, such as other esters and salts, free acids and neutral compounds, as well as isomers, in particular optical isomers, especially one or more commercially available forms. The chemical name given to a compound means at least one compound encompassed by the generic name, and generally the preferred compound.

For use, the formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compounds of the formula I required varies with the external conditions, such as temperature, humidity, the nature of the herbicide used and the like. It can vary within wide limits, for example between 0.001 and 1.0 kg a.i./ha or more of active substance, but it is preferably between 0.005 and 750 g a.i./ha, in particular between 0.005 and 500 g a.i./ha.

SPECIFIC MODE FOR CARRYING OUT THE INVENTION

The following examples are intended to illustrate the present invention and should not be construed as limiting the present invention in any way. The scope for which protection is sought in the present invention is intended to be defined by the claims.

In view of economics and variety of a compound, we preferably synthesized several compounds, part of which are listed in the following Table 1. The structure and information of a certain compound are shown in Tables 1-2. The compounds in Table 1 are listed for further explication of the present invention, other than any limit therefor. The subject of the present invention should not be interpreted by those skilled in the art as being limited to the following compounds.

TABLE 1

The structure of compounds

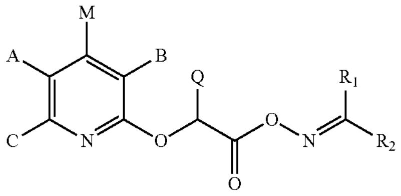

I

| No. | A | B | C | Q | $R_1$ | $R_2$ | M |
|---|---|---|---|---|---|---|---|
| 1 | F | F | F | $CH_3$ | Me | Me | $NH_2$ |
| 2 | Cl | Cl | Cl | $CH_3$ | Me | Ph | $NH_2$ |
| 3 | Cl | Cl | H | $CH_3$ | Ph | Ph | $NH_2$ |
| 4 | Cl | Cl | F | $CH_3$ | Me | Ph | $NH_2$ |
| 5 | Cl | Cl | $CH_3$ | $CH_3$ | Me | Ph | $NH_2$ |
| 6 | Cl | Cl | $CF_3$ | $CH_3$ | Me | Ph | $NH_2$ |
| 7 | $CH_3$ | $CH_3$ | F | $CH_3$ | Me | Ph | $NH_2$ |
| 8 | Et | Et | $CF_3$ | $CH_3$ | Me | Ph | $NH_2$ |
| 9 | 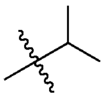 [SMILES: *C(C)C] | Cl | H | $CH_3$ | Ph | Ph | $NH_2$ |
| 10 | 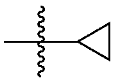 [SMILES: *C1CC1] | Cl | Cl | $CH_3$ | Me | Ph | $NH_2$ |
| 11 | F | 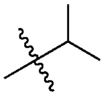 [SMILES: *C(C)C] | $CF_3$ | $CH_3$ | Me | Ph | $NH_2$ |
| 12 | Br | Br | F | $CH_3$ | Me | Ph | $NH_2$ |
| 13 | I | I | H | $CH_3$ | Ph | Ph | $NH_2$ |
| 14 | 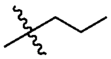 [SMILES: *CCC] | 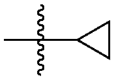 [SMILES: *C1CC1] | F | $CH_3$ | Me | Ph | $NH_2$ |
| 15 | $CF_3$ | Cl | F | $CH_3$ | Me | Me | $NH_2$ |
| 16 | Cl | $CF_3$ | H | $CH_3$ | Me | Me | $NH_2$ |
| 17 | Cl | Cl | I | $CH_3$ | Me | $—CH(CH_3)_2$ | $NH_2$ |
| 18 | Cl | 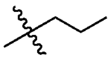 | Br | $CH_3$ | Ph | Ph | $NH_2$ |
| 19 | $CH_3$ | $CH_3$ | $CH_3$ | $CH_3$ | Me | $CH_2CH_2Cl$ | $NH_2$ |
| 20 | Cl | $CH_3$ | F | $CH_3$ | Me | Me | $NH_2$ |
| 21 | Cl | $CH_3$ | H | $CH_3$ | Me | Me | $NH_2$ |
| 22 | Cl | 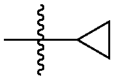 [SMILES: *C1CC1] | F | $CH_3$ | Me | Me | $NH_2$ |
| 23 | Cl | Cl | H | $CH_3$ | Me | Me | $NH_2$ |
| 24 | Cl | Cl | Cl | $CH_3$ | Me | Me | $NH_2$ |
| 25 | Cl | Cl | F | Et | Me | Ph | $NH_2$ |
| 26 | Cl | Cl | F | 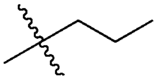 [SMILES: *CCC] | Me | Ph | $NH_2$ |
| 27 | Cl | Cl | F | 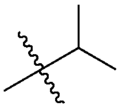 [SMILES: *C(C)C] | Me | Et | $NH_2$ |

TABLE 1-continued
The structure of compounds
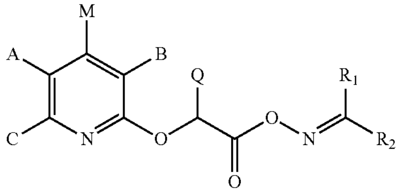
I
| No. | A | B | C | Q | $R_1$ | $R_2$ | M |
|---|---|---|---|---|---|---|---|
| 28 | Cl | Cl | F | 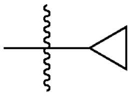 [SMILES: *C1CC1] | Me | $—CH_2CH_2CH_3$ | $NH_2$ |
| 29 | Cl | Cl | F | 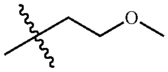 [SMILES: *CCOC] | Ph | Ph | $NH_2$ |
| 30 | Cl | Cl | F | 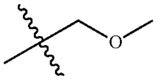 [SMILES: *COC] | Me | Ph | $NH_2$ |
| 31 | Cl | Cl | F | 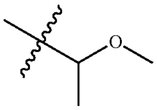 [SMILES: *C(C)OC] | Me | $—C(CH_3)_3$ | $NH_2$ |
| 32 | Cl | Cl | F | 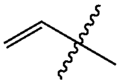 [SMILES: *C=C] | Me | Me | $NH_2$ |
| 33 | Cl | Cl | F | 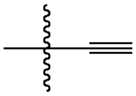 | Me | Me | $NH_2$ |
| 34 | Cl | Cl | F | F | Me | Me | $NH_2$ |
| 35 | Cl | Cl | F | Cl | Me | Me | $NH_2$ |
| 36 | Cl | Cl | F | Br | Me | Me | $NH_2$ |
| 37 | Cl | Cl | F | 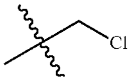 [SMILES: *CCl] | Me | Me | $NH_2$ |
| 38 | Cl | Cl | F | 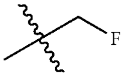 [SMILES: *CF] | Me | Me | $NH_2$ |
| 39 | Cl | Cl | F | 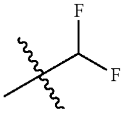 [SMILES: *C(F)F] | Me | Me | $NH_2$ |
| 40 | Cl | Cl | F | 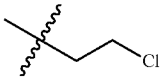 [SMILES: *CCCl] | Me | Me | $NH_2$ |
| 41 | Cl | Cl | F | $CF_3$ | Me | Me | $NH_2$ |
| 42 | Cl | Cl | F | 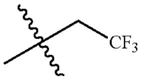 | Me | Me | $NH_2$ |
| 43 | Cl | Cl | F | CN | Me | Me | $NH_2$ |

TABLE 1-continued
The structure of compounds
I
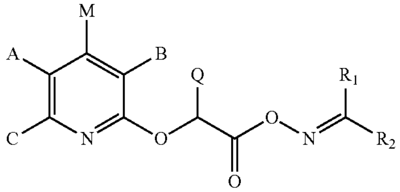
| No. | A | B | C | Q | $R_1$ | $R_2$ | M |
|---|---|---|---|---|---|---|---|
| 44 | Cl | Cl | F | 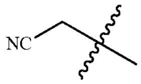 [SMILES: *CC#N] | Me | Me | $NH_2$ |
| 45 | Cl | Cl | F | $NH_2$ | Me | Me | $NH_2$ |
| 46 | Cl | Cl | F | 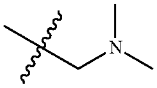 [SMILES: *CN(C)C] | Me | Me | $NH_2$ |
| 47 | Cl | Cl | F | 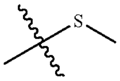 | Me | Me | $NH_2$ |
| 48 | Cl | Cl | F | 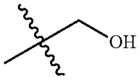 [SMILES: *CO] | Me | Me | $NH_2$ |
| 49 | Cl | Cl | F | $NO_2$ | Me | Me | $NH_2$ |
| 50 | Cl | Cl | F | 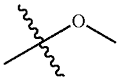 [SMILES: *OC] | Me | Me | $NH_2$ |
| 51 | Cl | Cl | F | 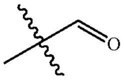 [SMILES: *C=O] | Me | Me | $NH_2$ |
| 52 | Cl | Cl | F | 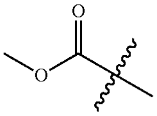 [SMILES: *C(=O)OC] | Me | Me | $NH_2$ |
| 53 | Cl | Cl | F | 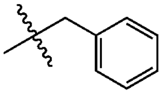 [SMILES: *Cc1ccccc1] | Me | Me | $NH_2$ |
| 54 | Cl | Cl | F | 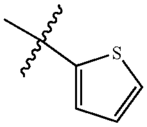 [SMILES: *c1cccs1] | Me | Me | $NH_2$ |
| 55 | Cl | Cl | F | 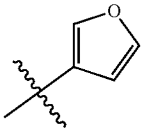 [SMILES: *c1ccoc1] | Me | Me | $NH_2$ |

TABLE 1-continued
The structure of compounds
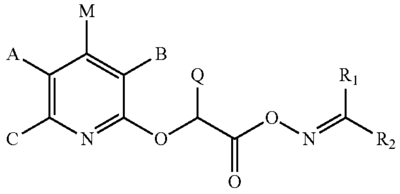
I
| No. | A | B | C | Q | $R_1$ | $R_2$ | M |
|---|---|---|---|---|---|---|---|
| 56 | Cl | Cl | F | 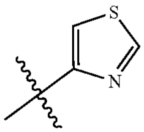 [SMILES: *c1cscn1] | Me | Me | $NH_2$ |
| 57 | Cl | Cl | F | 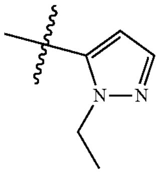 [SMILES: *c1ccnn1CC] | Me | Me | $NH_2$ |
| 58 | Cl | Cl | F | 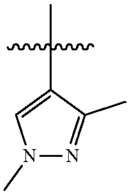 | Me | Me | $NH_2$ |
| 59 | Cl | Cl | F | 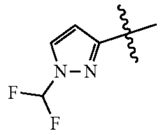 [SMILES: *c1ccn(C(F)F)n1] | Me | Me | $NH_2$ |
| 60 | Cl | Cl | F | 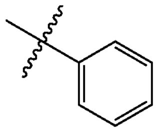 [SMILES: *c1ccccc1] | Me | Ph | $NH_2$ |
| 61 | Cl | Cl | F | 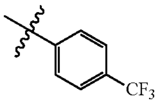 | Me | OEt | $NH_2$ |
| 62 | Cl | Cl | F | 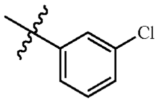 [SMILES: *c1cccc(Cl)c1] | H | H | $NH_2$ |
| 63 | Cl | Cl | F | 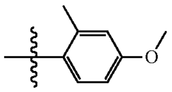 [SMILES: *c1ccc(OC)cc1C] | H | Et | $NH_2$ |
| 64 | Cl | Cl | F | 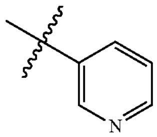 [SMILES: *c1cccnc1] | Me | Me | $NH_2$ |

TABLE 1-continued

The structure of compounds

I

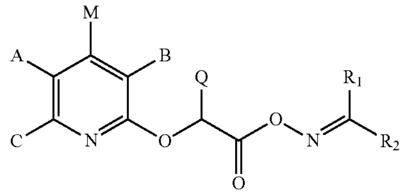

| No. | A | B | C | Q | $R_1$ | $R_2$ | M |
|---|---|---|---|---|---|---|---|
| 65 | Cl | Cl | F | 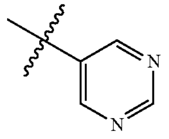 [SMILES: *c1cncnc1] | Me | Me | $NH_2$ |
| 66 | Cl | Cl | F | 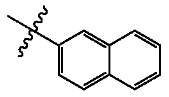 [SMILES: *c1ccc2ccccc2c1] | Et | Et | $NH_2$ |
| 67 | Cl | Cl | F | $CH_3$ | Me | Me | $NH_2$ |
| 68 | Cl | Cl | F | $CH_3$ | Et | $-CH(CH_3)_2$ | $NH_2$ |
| 69 | Cl | Cl | F | $CH_3$ | Et | n-Bu | $NH_2$ |
| 70 | Cl | Cl | F | $CH_3$ | Me | 4-Cl, Ph | $NH_2$ |
| 71 | Cl | Cl | F | $CH_3$ | Me | 4-$NO_2$, Ph | $NH_2$ |
| 72 | Cl | Cl | F | $CH_3$ | H | Ph | $NH_2$ |
| 73 | Cl | Cl | F | $CH_3$ | H | 3-$NO_2$, Ph | $NH_2$ |
| 74 | Cl | Cl | F | $CH_3$ | Et | Ph | $NH_2$ |
| 75 | Cl | Cl | F | $CH_3$ | $CH_2CH_2CH_3$ | Cl | $NH_2$ |
| 76 | Cl | Cl | F | $CH_3$ | n-Bu | OEt | $NH_2$ |
| 77 | Cl | Cl | F | $CH_3$ | Ph | 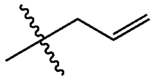 [SMILES: *CC=C] | $NH_2$ |
| 78 | Cl | Cl | F | $CH_3$ | Ph | Ph | $NH_2$ |
| 79 | Cl | Cl | F | $CH_3$ | Ph | 3-Cl, Ph | $NH_2$ |
| 80 | Cl | Cl | F | $CH_3$ | Ph | 4- 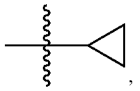 [SMILES: *C1CC1], Ph | $NH_2$ |
| 81 | Cl | Cl | F | $CH_3$ | 4-$CF_3$, Ph | Ph | $NH_2$ |
| 82 | Cl | Cl | F | $CH_3$ | 3-F, Ph | 4-Cl, Ph | $NH_2$ |
| 83 | Cl | Cl | F | $CH_3$ | 4-F, Ph | Ph | $NH_2$ |
| 84 | Cl | Cl | F | $CH_3$ | F | 2-OMe, Ph | $NH_2$ |
| 85 | Cl | Cl | F | $CH_3$ | Cl | 3-Et, Ph | $NH_2$ |
| 86 | Cl | Cl | F | $CH_3$ | Br | 4-CN, Ph | $NH_2$ |
| 87 | Cl | Cl | F | $CH_3$ | CN | 4-Cl, Ph | $NH_2$ |
| 88 | Cl | Cl | F | $CH_3$ | OEt | 4-NHCOMe, Ph | $NH_2$ |
| 89 | Cl | Cl | F | $CH_3$ | SMe | 4-SMe, Ph | $NH_2$ |
| 90 | Cl | Cl | F | $CH_3$ | $NO_2$ | 4-$N(Me)_2$, Ph | $NH_2$ |
| 91 | Cl | Cl | F | $CH_3$ | Ac | 4-NHOPh, Ph | $NH_2$ |

TABLE 1-continued

The structure of compounds

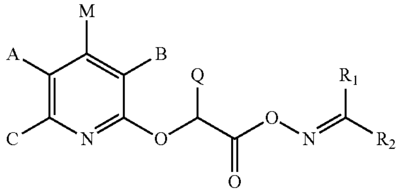

I

| No. | A | B | C | Q | $R_1$ | $R_2$ | M |
|---|---|---|---|---|---|---|---|
| 92 | Cl | Cl | F | $CH_3$ | COOEt | 4- 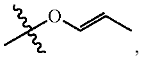 [SMILES: *O/C=C/C] , Ph | $NH_2$ |
| 93 | Cl | Cl | F | $CH_3$ | Bn | 2- $NH_2$, Ph | $NH_2$ |
| 94 | Cl | Cl | F | $CH_3$ | 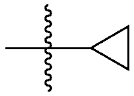 [SMILES: *C1CC1] | CONHBn | $NH_2$ |
| 95 | Cl | Cl | F | $CH_3$ | 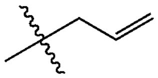 [SMILES: *CC=C] | 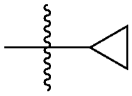 [SMILES: *C1CC1] | $NH_2$ |
| 96 | Cl | Cl | F | $CH_3$ | OPh | COOPh | $NH_2$ |
| 97 | Cl | Cl | F | $CH_3$ | SPh | COEt | $NH_2$ |
| 98 | Cl | Cl | F | $CH_3$ | CONHPr | Ph | $NH_2$ |
| 99 | Cl | Cl | F | $CH_3$ | $CON(Me)_2$ | Ph | $NH_2$ |
| 100 | Cl | Cl | F | $CH_3$ | 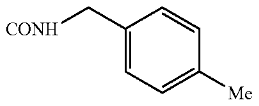 | Et | $NH_2$ |
| 101 | Cl | Cl | F | $CH_3$ | 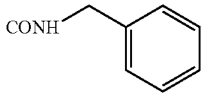 | Ph | $NH_2$ |
| 102 | Cl | Cl | F | $CH_3$ | 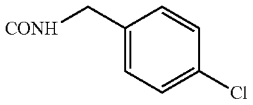 | COSMe | $NH_2$ |
| 103 | Cl | Cl | F | $CH_3$ | 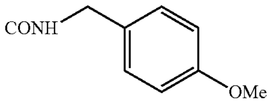 | Me | $NH_2$ |
| 104 | Cl | Cl | F | $CH_3$ | 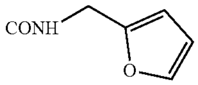 | Ph | $NH_2$ |
| 105 | Cl | Cl | F | $CH_3$ | 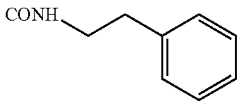 | Ph | $NH_2$ |
| 106 | Cl | Cl | F | $CH_3$ | 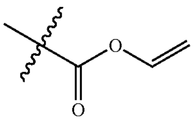 [SMILES: *C(=O)OC=C] | CONMePh | $NH_2$ |

TABLE 1-continued
The structure of compounds
I
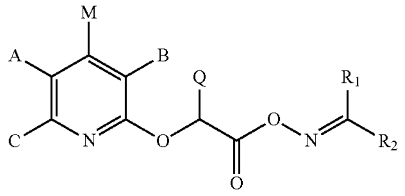
| No. | A | B | C | Q | $R_1$ | $R_2$ | M |
|---|---|---|---|---|---|---|---|
| 107 | Cl | Cl | F | $CH_3$ | 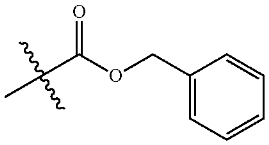 [SMILES: *C(=O)OCc1ccccc1] | Ph | $NH_2$ |
| 108 | Cl | Cl | F | $CH_3$ | 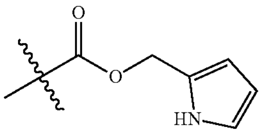 [SMILES: *C(=O)OCc1ccc[nH]1] | Et | $NH_2$ |
| 109 | Cl | Cl | F | $CH_3$ | 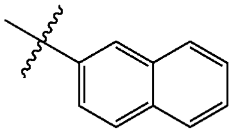 [SMILES: *c1ccc2ccccc2c1] | COOMe | $NH_2$ |
| 110 | Cl | Cl | F | $CH_3$ | $CH_3$ | $CH_3$ | 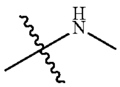 [SMILES: *NC] |
| 111 | Cl | Cl | F | $CH_3$ | $CH_3$ | $CH_3$ | 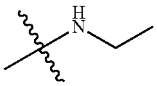 [SMILES: *NCC] |
| 112 | Cl | Cl | F | $CH_3$ | $CH_3$ | $CH_3$ | 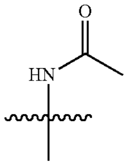 [SMILES: *NC(C)=O] |
| 113 | Cl | Cl | F | $CH_3$ | $CH_3$ | $CH_3$ | 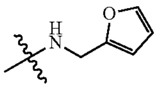 [SMILES: *NCc1ccco1] |
| 114 | Cl | Cl | F | $CH_3$ | $CH_3$ | $CH_3$ | 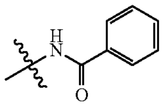 [SMILES: *NC(=O)c1ccccc1] |
| 115 | Cl | Cl | F | $CH_3$ | $CH_3$ | $CH_3$ | 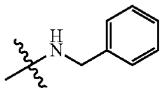 [SMILES: *NCc1ccccc1] |
| 116 | Cl | Cl | F | $CH_3$ | 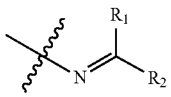 represents | | $NH_2$ |

TABLE 1-continued

The structure of compounds

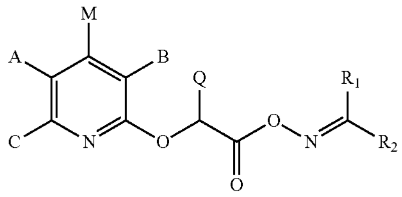

I

| No. | A | B | C | Q | $R_1$ | $R_2$ | M |
|---|---|---|---|---|---|---|---|
| | | | | | 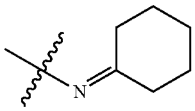 [SMILES: *N=C1CCCCC1] | | |
| 117 | Cl | Cl | F | $CH_3$ | 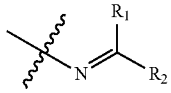 represents 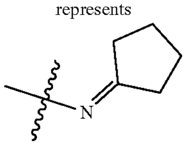 | | $NH_2$ |
| 118 | Cl | Cl | F | $CH_3$ | $CH_3$ | $CH_3$ | 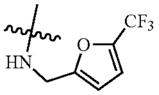 [SMILES: *NCc1ccc(C(F)(F)F)o1] |

TABLE 2

| No. | $^1$H NMR data of compounds $^1$H NMR |
|---|---|
| 1 | $^1$H NMR (500 MHz, DMSO-$d_6$) δ 6.36 (s, 2H), 4.49 (q, J = 7.0 Hz, 1H), 2.45 (s, 3H), 2.42 (s, 3H), 1.60 (d, J = 7.0 Hz, 3H). |
| 2 | $^1$H NMR (500 MHz, DMSO-$d_6$) δ 7.59-7.46 (m, 5H), 6.78 (s, 2H), 4.75 (q, J = 7.0 Hz, 1H), 2.74 (s, 3H), 1.57 (d, J = 7.0 Hz, 3H). |
| 3 | $^1$H NMR (500 MHz, DMSO-$d_6$) δ 7.65 (s, 1H), 7.54-7.50 (m, 2H), 7.45-7.34 (m, 8H), 6.83 (s, 2H), 4.65 (q, J = 7.0 Hz, 1H), 1.49 (d, J = 7.0 Hz, 3H). |
| 4 | $^1$H NMR (500 MHz, DMSO-$d_6$) δ 7.59-7.49 (m, 3H), 7.48 (dd, J = 7.5, 2.0 Hz, 2H), 6.78 (s, 2H), 4.71 (q, J = 7.0 Hz, 1H), 2.72 (s, 3H), 1.58 (d, J = 7.0 Hz, 3H). |
| 5 | $^1$H NMR (500 MHz, DMSO-$d_6$) δ 7.59-7.46 (m, 5H), 6.71 (s, 2H), 4.71 (q, J = 7.0 Hz, 1H), 2.79 (s, 3H), 2.53 (s, 3H), 1.51 (d, J = 7.0 Hz, 3H). |
| 6 | $^1$H NMR (500 MHz, DMSO-$d_6$) δ 7.59-7.48 (m, 5H), 6.82 (s, 2H), 4.68 (q, J = 7.0 Hz, 1H), 2.87 (s, 3H), 1.48 (d, J = 7.0 Hz, 3H). |
| 7 | $^1$H NMR (500 MHz, DMSO-$d_6$) δ 7.55-7.46 (m, 5H), 6.36 (s, 2H), 4.48 (q, J = 7.0 Hz, 1H), 2.79 (s, 3H), 2.14 (s, 3H), 2.01 (s, 3H), 1.56 (d, J = 7.0 Hz, 3H). |
| 8 | $^1$H NMR (500 MHz, DMSO-$d_6$) δ 7.59-7.46 (m, 5H), 6.36 (s, 2H), 4.76 (q, J = 7.0 Hz, 1H), 2.74 (s, 3H), 2.71-2.68 (m, 1H), 2.55-2.49 (m, 1H), 2.16-2.05 (m, 1H), 2.00-1.94 (m, 1H), 1.59 (d, J = 7.0 Hz, 3H), 1.13-1.10 (m, 6H). |
| 9 | $^1$H NMR (500 MHz, DMSO-$d_6$) δ 7.58-7.48 (m, 11H), 6.36 (s, 2H), 4.70 (q, J = 7.0 Hz, 1H), 2.90-2.85 (m, 1H), 1.52 (d, J = 7.0 Hz, 3H), 1.19-1.12 (m, 6H). |
| 10 | $^1$H NMR (500 MHz, DMSO-$d_6$) δ 7.59-7.48 (m, 5H), 6.36 (s, 2H), 4.72 (q, J = 7.0 Hz, 1H), 2.89 (s, 3H), 2.08-2.03 (m, 1H), 1.47 (d, J = 6.5 Hz, 3H), 0.99-0.90 (m, 2H), 0.78-0.68 (m, 2H). |
| 11 | $^1$H NMR (500 MHz, DMSO-$d_6$) δ 7.59-7.47 (m, 5H), 6.36 (s, 2H), 4.71 (q, J = 7.0 Hz, 1H), 3.22-3.17 (m, 1H), 2.86 (s, 3H), 1.50 (d, J = 7.0 Hz, 3H), 1.13-1.06 (m, 6H). |
| 12 | $^1$H NMR (500 MHz, DMSO-$d_6$) δ 7.59-7.48 (m, 5H), 6.62 (s, 2H), 4.69 (q, J = 7.0 Hz, 1H), 2.87 (s, 3H), 1.48 (d, J = 7.0 Hz, 3H). |
| 13 | $^1$H NMR (500 MHz, DMSO-$d_6$) δ 8.02 (s, 1H), 7.54-7.36 (m, 10H), 6.36 (s, 2H), 4.06 (q, J = 7.0 Hz, 1H), 1.34 (d, J = 7.0 Hz, 3H). |
| 14 | $^1$H NMR (500 MHz, DMSO-$d_6$) δ 7.59-7.48 (m, 5H), 6.36 (s, 2H), 4.71 (q, J = 7.0 Hz, 1H), 2.80 (s, 3H), 2.62 (t, J = 8.0 Hz, 2H), 2.02-1.98 (m, 1H), 1.64 (q, J = 8.0 Hz, 2H), 1.48 (d, J = 7.0 Hz, 3H), 1.07-1.00 (m, 2H), 0.94 (t, J = 8.0 Hz, 3H), 0.78-0.71 (m, 2H). |
| 15 | $^1$H NMR (500 MHz, DMSO-$d_6$) δ 6.36 (s, 2H), 4.57 (q, J = 7.0 Hz, 1H), 2.48 (s, 3H), 2.45 (s, 3H), 1.54 (d, J = 7.0 Hz, 3H). |
| 16 | $^1$H NMR (500 MHz, DMSO-$d_6$) δ 7.72 (s, 1H), 6.36 (s, 2H), 4.64 (q, J = 7.0 Hz, 1H), 2.35 (s, 3H), 2.30 (s, 3H), 1.47 (d, J = 7.0 Hz, 3H). |

TABLE 2-continued

| No. | $^1$H NMR data of compounds<br>$^1$H NMR |
|---|---|
| 17 | $^1$H NMR (500 MHz, DMSO-$d_6$) δ 6.53 (s, 2H), 4.60 (q, J = 7.0 Hz, 1H), 2.42 (s, 3H), 1.76-1.72 (m, 1H), 1.50 (d, J = 7.0 Hz, 3H), 0.99-0.92 (m, 6H). |
| 18 | $^1$H NMR (500 MHz, DMSO-$d_6$) δ7.54-7.50 (m, 2H), 7.48-7.40 (m, 2H), 7.44-7.34 (m, 6H), 6.36 (s, 2H), 4.65 (q, J = 7.0 Hz, 1H), 2.28-2.23 (m, 1H), 1.83-1.78 (m, 1H), 1.63-1.56 (m, 1H), 1.53 (d, J = 7.0 Hz, 3H), 1.53-1.40 (m, 1H), 0.94 (t, J = 8.0 Hz, 3H). |
| 19 | $^1$H NMR (500 MHz, DMSO-$d_6$) δ 6.36 (s, 2H), 4.46 (q, J = 7.0 Hz, 1H), 3.35-3.29 (m, 1H), 3.22-3.16 (m, 1H), 2.84-2.78 (m, 1H), 2.53 (s, 3H), 2.40 (s, 3H), 2.17-2.11 (m, 4H), 2.03 (s, 3H), 1.59 (d, J = 7.0 Hz, 3H). |
| 20 | $^1$H NMR (500 MHz, DMSO-$d_6$) δ 6.36 (s, 2H), 4.47 (q, J = 7.0 Hz, 1H), 2.48 (s, 3H), 2.44 (s, 3H), 2.07 (s, 3H), 1.40 (d, J = 7.0 Hz, 3H). |
| 21 | $^1$H NMR (500 MHz, DMSO-$d_6$) δ 7.49 (s, 1H), 6.36 (s, 2H), 4.46 (q, J = 7.0 Hz, 1H), 2.45 (s, 3H), 2.43 (s, 3H), 2.07 (s, 3H), 1.60 (d, J = 7.0 Hz, 3H). |
| 22 | $^1$H NMR (500 MHz, DMSO-$d_6$) δ 6.36 (s, 2H), 4.49 (q, J = 7.0 Hz, 1H), 2.45 (s, 3H), 2.43 (s, 3H), 2.02 (p, J = 7.0 Hz, 1H), 1.45 (d, J = 7.0 Hz, 3H), 0.96-0.93 (m, 2H), 0.74-0.65 (m, 2H). |
| 23 | $^1$H NMR(500 MHz, DMSO-$d_6$) δ 7.60 (s, 1H), 6.79 (s, 2H), 4.68 (q, J = 7.0 Hz, 1H), 2.43 (s, 3H), 2.41 (s, 3H), 1.52 (d, J = 7.0 Hz, 3H). |
| 24 | $^1$H NMR (500 MHz, DMSO-$d_6$) δ 6.81 (s, 2H), 4.74 (q, J = 7.0 Hz, 1H), 2.42 (s, 3H), 2.39 (s, 3H), 1.47 (d, J = 7.0 Hz, 3H). |
| 25 | $^1$H NMR (500 MHz, DMSO-$d_6$) δ 7.59-7.49 (m, 3H), 7.49-7.42 (m, 2H), 6.77 (s, 2H), 4.29 (dd, J = 11.0, 1.0 Hz, 1H), 2.88 (s, 3H), 2.08-1.99 (m, 1H), 1.61-1.47 (m, 1H), 0.83 (t, J = 8.0 Hz, 3H). |
| 26 | $^1$H NMR (500 MHz, DMSO-$d_6$) δ7.59-7.48(m, 5H), 6.77 (s, 2H), 4.33 (dd, J = 11.0, 1.0 Hz, 1H), 2.89 (s, 3H), 1.90-1.79 (m, 1H), 1.66-1.53 (m, 1H), 1.54-1.40 (m, 2H), 0.81 (t, J = 8.0 Hz, 3H). |
| 27 | $^1$H NMR (500 MHz, DMSO-$d_6$) δ 6.80 (s, 2H), 4.37 (d, J = 7.0 Hz, 1H), 2.82-2.75 (m, 1H), 2.44 (s, 3H), 2.41-2.33 (m, 1H), 1.86-1.82 (m, 1H), 0.95-0.88 (m, 6H), 0.86 (d, J = 7.0 Hz, 3H). |
| 28 | $^1$H NMR (500 MHz, DMSO-$d_6$) δ 6.77 (s, 2H), 3.48 (d, J = 7.0 Hz, 1H), 2.56-2.50 (m, 1H), 2.40 (s, 3H), 1.97-1.86 (m, 1H), 1.11-1.06 (m, 1H), 1.10-0.96 (m, 1H), 0.92-0.85 (m, 4H), 0.48-0.43 (m, 2H), 0.32-0.27 (m, 2H). |
| 29 | $^1$H NMR (500 MHz, DMSO-$d_6$) δ 7.54-7.50 (m, 2H), 7.47-7.33 (m, 8H), 6.82 (s, 2H), 4.26 (dd, J = 11.0, 1.5 Hz, 1H), 3.55-3.49 (m, 1H), 3.20-3.15 (m, 5H), 1.31-1.26 (m, 1H), 0.80-0.72 (m, 1H). |
| 30 | $^1$H NMR (500 MHz, DMSO-$d_6$) δ 7.57-7.51 (m, 3H), 7.47 (dd, J = 7.5, 2.5 Hz, 2H), 6.79 (s, 2H), 4.41 (t, J = 7.0 Hz, 1H), 4.18 (dd, J = 12.5, 7.0 Hz, 1H), 3.83 (dd, J = 12.5, 7.0 Hz, 1H), 3.29 (s, 3H), 2.72 (s, 3H). |
| 31 | $^1$H NMR (500 MHz, DMSO-$d_6$) δ 6.79 (s, 2H), 4.36 (d, J = 7.0 Hz, 1H), 3.89 (p, J = 7.0 Hz, 1H), 3.20 (s, 3H), 2.57 (s, 3H), 1.15 (d, J = 7.0 Hz, 3H), 1.06 (s, 9H). |
| 32 | $^1$H NMR (500 MHz, DMSO-$d_6$) δ 6.81 (s, 2H), 6.38-6.32 (m, 1H), 5.37-5.28 (m, 1H), 5.31-5.21 (m, 1H), 5.19 (dd, J = 6.0, 1.0 Hz, 1H), 2.41(s, 3H), 2.38 (s, 3H). |
| 33 | $^1$H NMR (500 MHz, DMSO-$d_6$) δ 6.80 (s, 2H), 5.69 (d, J = 3.5 Hz, 1H), 3.68 (d, J = 3.0 Hz, 1H), 2.53 (s, 3H), 2.51 (s, 3H) |
| 34 | $^1$H NMR (500 MHz, DMSO-$d_6$) δ 7.01 (d, J = 46.5 Hz, 1H), 6.81 (s, 2H), 2.45 (s, 3H), 2.43 (s, 3H) |
| 35 | $^1$H NMR (500 MHz, DMSO-$d_6$) δ 6.81 (s, 2H), 6.65 (s, 1H), 2.45 (s, 3H), 2.43 (s, 3H). |
| 36 | $^1$H NMR (500 MHz, DMSO-$d_6$) δ 6.84 (s, 2H), 6.78 (s, 1H), 2.45 (s, 3H), 2.43 (s, 3H). |
| 37 | $^1$H NMR (500 MHz, DMSO-$d_6$) δ 6.81 (s, 2H), 4.58 (t, J = 7.0 Hz, 1H), 4.33 (dd, J = 12.5, 7.0 Hz, 1H), 4.09 (dd, J = 12.5, 7.0 Hz, 1H), 2.45 (s, 3H), 2.42 (s, 3H). |
| 38 | $^1$H NMR (500 MHz, DMSO-$d_6$) δ 6.80 (s, 2H), 5.28-4.93 (m, 2H), 4.72-4.64 (m, 1H), 2.45 (s, 3H), 2.43 (s, 3H) |
| 39 | $^1$H NMR (500 MHz, DMSO-$d_6$) δ 6.78 (s, 2H), 6.26-6.02 (m, 1H), 5.18-5.08 (m, 1H), 2.45 (s, 3H), 2.43 (s, 3H). |
| 40 | $^1$H NMR (500 MHz, DMSO-$d_6$) δ 6.85 (s, 2H), 4.24 (d, J = 9.5 Hz, 1H), 3.93-3.87 (m, 1H), 3.72-3.66 (m, 1H), 2.43-2.37 (m, 7H), 1.96-1.91 (m, 1H). |
| 41 | $^1$H NMR (500 MHz, DMSO-$d_6$) δ 6.83 (s, 2H), 5.51 (q, J = 9.0 Hz, 1H), 2.45 (s, 3H), 2.42 (s, 3H). |
| 42 | $^1$H NMR (500 MHz, DMSO-$d_6$) δ 6.80 (s, 2H), 4.58-4.52 (m, 1H), 3.21-3.13 (m, 1H), 2.43 (s, 3H), 2.40 (s, 3H), 2.11-2.03 (m, 1H). |
| 43 | $^1$H NMR (500 MHz, DMSO-$d_6$) δ 6.82 (s, 2H), 5.83 (s, 1H), 2.44 (s, 3H), 2.41 (s, 3H). |
| 44 | $^1$H NMR (500 MHz, DMSO-$d_6$) δ 6.81 (s, 2H), 4.87 (t, J = 7.0 Hz, 1H), 3.45 (dd, J = 12.5, 7.0 Hz, 1H), 2.83 (dd, J = 12.5, 7.0 Hz, 1H), 2.44 (s, 3H), 2.40 (s, 3H). |
| 45 | $^1$H NMR (500 MHz, DMSO-$d_6$) δ 6.82 (s, 2H), 5.87 (s, 1H), 2.43 (s, 3H), 2.39 (s, 3H). 2.33 (s, 2H). |
| 46 | $^1$H NMR (500 MHz, DMSO-$d_6$) δ 6.85 (s, 2H), 4.52 (t, J = 7.0 Hz, 1H), 3.04 (dd, J = 12.5, 7.0 Hz, 1H), 2.71 (dd, J = 12.5, 7.0 Hz, 1H), 2.45 (s, 3H), 2.43 (s, 3H). 2.17 (s, 6H). |
| 47 | $^1$H NMR (500 MHz, DMSO-$d_6$) δ 6.80 (s, 2H), 5.76 (s, 1H), 2.49 (s, 3H), 2.47 (s, 3H). 2.17 (s, 3H). |
| 48 | $^1$H NMR (500 MHz, DMSO-$d_6$) δ 6.81 (s, 2H), 4.97 (t, J = 5.5 Hz, 1H), 4.44-4.39 (m, 1H), 4.18 (t, J = 7.0 Hz, 1H), 3.85-3.80 (m, 1H), 2.45 (s, 3H), 2.43 (s, 3H). |
| 49 | $^1$H NMR (500 MHz, DMSO-$d_6$) δ 7.28 (s, 1H), 6.80 (s, 2H), 2.45 (s, 3H), 2.43 (s, 3H) .. |
| 50 | $^1$H NMR (500 MHz, DMSO-$d_6$) δ 6.81 (s, 2H), 6.08 (s, 1H), 3.26 (s, 3H), 2.48 (s, 3H), 2.46 (s, 3H). |
| 51 | $^1$H NMR (500 MHz, DMSO-$d_6$) δ 10.11 (d, J = 6.0 Hz, 1H), 6.79 (s, 2H), 5.41 (d, J = 6.0 Hz, 1H), 2.45 (s, 3H), 2.43 (s, 3H). |
| 52 | $^1$H NMR (500 MHz, DMSO-$d_6$) δ 6.80 (s, 2H), 5.61 (s, 1H), 3.65 (s, 3H), 2.48 (s, 3H), 2.46 (s, 3H). |
| 53 | $^1$H NMR (500 MHz, DMSO-$d_6$) δ 7.32-7.30 (m, 2H), 7.28-7.15 (m, 3H), 6.77 (s, 2H), 4.81 (t, J = 7.0 Hz, 1H), 3.24-3.15 (m, 1H), 2.98-2.89 (m, 1H), 2.35 (s, 3H), 2.32 (s, 3H). |
| 54 | $^1$H NMR (500 MHz, DMSO-$d_6$) δ 7.40 (dd, J = 7.5, 2.0 Hz, 1H), 7.19 (dd, J = 7.5, 1.5 Hz, 1H), 7.05 (t, J = 7.5 Hz, 1H), 6.80 (s, 2H), 6.24 (s, 1H), 2.53 (s, 3H), 2.50 (s, 3H) .. |
| 55 | $^1$H NMR (500 MHz, DMSO-$d_6$) δ 7.47 (d, J = 7.5 Hz, 1H), 7.41 (d, J = 1.5 Hz, 1H), 6.81 (s, 2H), 6.37 (dd, J = 7.5, 1.5 Hz, 1H), 6.07 (s, 1H), 2.51 (s, 3H), 2.50 (s, 3H). |
| 56 | $^1$H NMR (500 MHz, DMSO-$d_6$) δ 8.86 (s, 1H), 7.42-7.40 (m, 1H), 6.81 (s, 2H), 6.07 (s, 1H), 2.52 (s, 3H), 2.50 (s, 3H). |
| 57 | $^1$H NMR (500 MHz, DMSO-$d_6$) δ 7.58 (d, J = 7.5 Hz, 1H), 6.80 (s, 2H), 6.52 (d, J = 7.5 Hz, 1H), 5.98 (s, 1H), 4.70-4.62 (m, 1H), 4.26-4.19 (m, 1H), 2.53 (s, 3H), 2.51 (s, 3H), 1.26 (t, J = 8.0 Hz, 3H). |

TABLE 2-continued

| No. | $^1H$ NMR data of compounds $^1H$ NMR |
|---|---|
| 58 | $^1H$ NMR (500 MHz, DMSO-d6) δ 7.11 (s, 1H), 6.81 (s, 2H), 6.08 (s, 1H), 3.72 (s, 3H), 2.49 (s, 3H), 2.46 (s, 3H), 2.33 (s, 3H). |
| 59 | $^1H$ NMR (500 MHz, DMSO-$d_6$) δ 7.83 (t, J = 57.5 Hz, 1H), 7.34 (d, J = 7.5 Hz, 1H), 6.80 (s, 2H), 6.52 (d, J = 7.5 Hz, 1H), 6.28 (s, 1H), 2.51 (s, 3H), 2.49(s, 3H) |
| 60 | $^1H$ NMR (500 MHz, DMSO-$d_6$) δ 7.74-7.67 (m, 2H), 7.59-7.39 (m, 8H), 6.81 (s, 2H), 5.93 (d, J = 1.5 Hz, 1H), 2.85 (s, 3H). |
| 61 | $^1H$ NMR (500 MHz, DMSO-$d_6$) δ 7.79-7.77 (m, 2H), 7.44-7.41 (m, 2H), 7.37-7.29 (m, 1H), 6.75 (s, 2H), 5.86 (d, J = 1.0 Hz, 1H), 4.01-3.83 (m, 2H), 2.10 (s, 3H), 1.36 (t, J = 8.0 Hz, 3H). |
| 62 | $^1H$ NMR (500 MHz, DMSO-$d_6$) δ 7.99-7.94 (m, 1H), 7.59-7.57 (m, 1H), 7.43-7.32 (m, 2H), 6.84 (s, 2H), 5.98 (d, J = 2.0 Hz, 1H), 5.90 (d, J = 2.0 Hz, 1H), 5.82 (d, J = 1.0 Hz, 1H). |
| 63 | $^1H$ NMR (500 MHz, DMSO-$d_6$) δ 7.43 (dd, J = 7.5, 1.0 Hz, 1H), 6.92 (dd, J = 7.5, 2.0 Hz, 1H), 6.77 (s, 2H), 6.74-6.69 (m, 1H), 6.30 (dd, J = 10.0, 3.5 Hz, 1H), 5.82 (d, J = 1.0 Hz, 1H), 3.72 (s, 3H), 2.46-2.36 (m, 1H), 2.13 (d, J = 1.0 Hz, 3H), 1.91-1.83 (m, 1H), 0.96 (t, J = 8.0 Hz, 3H). |
| 64 | $^1H$ NMR (500 MHz, DMSO-$d_6$) δ 8.71 (d, J = 1.0 Hz, 1H), 8.40 (dd, J = 5.0, 1.0 Hz, 1H), 7.73 (dt, J = 8.0, 1.0 Hz, 1H), 7.51 (dd, J = 8.0, 5.0 Hz, 1H), 6.77 (s, 2H), 5.91 (s, 1H), 2.43 (s, 3H), 2.41 (s, 3H). |
| 65 | $^1H$ NMR (500 MHz, DMSO-$d_6$) δ 9.12 (s, 1H), 8.83 (s, 2H), 6.77 (s, 2H), 5.78 (s, 1H), 2.45 (s, 3H), 2.43 (s, 3H). |
| 66 | $^1H$ NMR (500 MHz, DMSO-$d_6$) δ 8.14 (s, 1H), 8.06-8.04 (m, 1H), 8.02-7.91 (m, 2H), 7.81 (dd, J = 7.0, 1.5 Hz, 1H), 7.58-7.55 (m, 2H), 6.18 (s, 2H), 6.10 (s, 1H), 2.65-2.63 (m, 2H), 2.33-2.31 (m, 2H), 0.96-0.98 (m, 6H). |
| 67 | $^1H$ NMR (500 MHz, DMSO-$d_6$) δ 6.79 (s, 2H), 4.73 (q, J = 7.0 Hz, 1H), 2.47 (s, 3H), 2.41 (s, 3H), 1.50 (d, J = 7.0 Hz, 3H). |
| 68 | $^1H$ NMR (500 MHz, DMSO-$d_6$) δ 6.81 (s, 2H), 4.70 (q, J = 7.0 Hz, 1H), 2.87-2.85 (m, 1H), 2.00-1.84 (m, 2H), 1.47 (d, J = 7.0 Hz, 3H), 0.96 (d, J = 7.0 Hz, 3H), 0.91 (d, J = 7.0 Hz, 3H), 0.86 (t, J = 8.0 Hz, 3H). |
| 69 | $^1H$ NMR (500 MHz, DMSO-$d_6$) δ 6.81 (s, 2H), 4.69 (q, J = 7.0 Hz, 1H), 3.17-3.12 (m, 1H), 2.58-2.51 (m, 1H), 2.03-1.96 (m, 1H), 1.76-1.71 (m, 1H), 1.50 (d, J = 7.0 Hz, 3H), 1.46-1.38 (m, 1H), 1.27-1.06 (m, 2H), 0.94-0.88 (m, 6H), 0.77-0.64 (m, 1H). |
| 70 | $^1H$ NMR (500 MHz, DMSO-$d_6$) δ 7.65-7.59 (m, 2H), 7.46-7.39 (m, 2H), 6.80 (s, 2H), 4.63 (q, J = 7.0 Hz, 1H), 2.72 (s, 3H), 1.36 (d, J = 7.0 Hz, 3H). |
| 71 | $^1H$ NMR (500 MHz, DMSO-$d_6$) δ 8.35-8.28 (m, 2H), 7.65-7.59 (m, 2H), 6.79 (s, 2H), 4.70 (q, J = 7.0 Hz, 1H), 2.76 (s, 3H), 1.51 (d, J = 7.0 Hz, 3H). |
| 72 | $^1H$ NMR (500 MHz, DMSO-$d_6$) δ 7.83 (s, 1H), 7.69-7.62 (m, 2H), 7.59-7.56 (m, 1H), 7.44-7.42 (m, 2H), 6.78 (s, 2H), 4.70 (q, J = 7.0 Hz, 1H), 1.45 (d, J = 7.0 Hz, 3H). |
| 73 | $^1H$ NMR (500 MHz, DMSO-$d_6$) δ 8.36-8.30 (m, 2H), 7.75-7.66 (m, 3H), 6.81 (s, 2H), 4.69 (q, J = 6.9 Hz, 1H), 1.43 (d, J = 7.0 Hz, 3H). |
| 74 | $^1H$ NMR (500 MHz, DMSO-$d_6$) δ 7.56-7.49 (m, 5H), 6.79 (s, 2H), 4.64 (q, J = 7.0 Hz, 1H), 2.61-2.54 (m, 1H), 2.30-2.22 (m, 1H), 1.45 (d, J = 7.0 Hz, 3H), 1.01 (t, J = 8.0 Hz, 3H). |
| 75 | $^1H$ NMR (500 MHz, DMSO-$d_6$) δ 6.83 (s, 2H), 4.69 (q, J = 7.0 Hz, 1H), 2.74-2.71 (m, 1H), 2.36-2.34 (m, 1H), 1.43 (d, J = 7.0 Hz, 3H), 1.31-1.22 (m, 1H), 0.87 (t, J = 8.0 Hz, 3H), 0.49-0.39 (m, 1H). |
| 76 | $^1H$ NMR (500 MHz, DMSO-$d_6$) δ 6.80 (s, 2H), 4.76 (q, J = 7.0 Hz, 1H), 4.02-3.90 (m, 2H), 2.90-2.84 (m, 1H), 2.33-2.28 (m, 1H), 1.74-1.64 (m, 1H), 1.45 (d, J = 6.5 Hz, 3H), 1.45-1.24 (m, 5H), 1.03-0.93 (m, 1H), 0.93 (t, J = 8.0 Hz, 3H). |
| 77 | $^1H$ NMR (500 MHz, DMSO-$d_6$) δ 7.59-7.49 (m, 5H), 6.77 (s, 2H), 5.99-5.91 (m, 1H), 5.18-5.14 (m, 1H), 5.10-5.00 (m, 1H), 4.61 (q, J = 7.0 Hz, 1H), 3.17-3.09 (m, 1H), 2.90-2.82 (m, 1H), 1.48 (d, J = 7.0 Hz, 3H). |
| 78 | $^1H$ NMR (500 MHz, DMSO-$d_6$) δ 7.56-7.47 (m, 2H), 7.47-7.39 (m, 6H), 7.37 (t, J = 7.5 Hz, 2H), 6.80 (s, 2H), 4.72 (q, J = 7.0 Hz, 1H), 1.38 (d, J = 7.0 Hz, 3H). |
| 79 | $^1H$ NMR (500 MHz, DMSO-$d_6$) δ 7.72 (t, J = 2.0 Hz, 1H), 7.58-7.47 (m, 2H), 7.43 (t, J = 7.5 Hz, 1H), 7.35-7.26 (m, 3H), 7.29-7.22 (m, 2H), 6.81 (s, 2H), 4.74 (q, J = 7.0 Hz, 1H), 1.53 (d, J = 7.0 Hz, 3H). |
| 80 | $^1H$ NMR (500 MHz, DMSO-$d_6$) δ 7.53-7.49 (m, 3H), 7.32-7.22 (m, 6H), 6.81 (s, 2H), 4.70 (q, J = 7.0 Hz, 1H), 2.29 (p, J = 7.0 Hz, 1H), 1.25 (d, J = 6.5 Hz, 3H), 1.12-1.08 (m, 2H), 0.84-0.80 (m, 2H). |
| 81 | $^1H$ NMR (500 MHz, DMSO-$d_6$) δ 7.72 (d, J = 7.0 Hz, 2H), 7.59-7.53 (m, 2H), 7.52-7.48 (m, 1H), 7.36-7.30 (m, 2H), 7.26 (t, J = 7.5 Hz, 2H), 6.80 (s, 2H), 4.71 (q, J = 7.0 Hz, 1H), 1.51 (d, J = 7.0 Hz, 3H). |
| 82 | $^1H$ NMR (500 MHz, DMSO-$d_6$) δ 7.84-7.78 (m, 2H), 7.64-7.57 (m, 2H), 7.56-7.52 (m, 1H), 7.49-7.40 (m, 2H), 7.36-7.33 (m, 1H), 6.80 (s, 2H), 4.65 (q, J = 7.0 Hz, 1H), 1.47 (d, J = 7.0 Hz, 3H). |
| 83 | $^1H$ NMR (500 MHz, DMSO-$d_6$) δ 7.53-7.52 (m, 1H), 7.50-7.43 (m, 2H), 7.37-7.30 (m, 2H), 7.29-7.22 (m, 2H), 7.21 (dd, J = 8.0, 2.0 Hz, 2H), 6.79 (s, 2H), 4.74 (q, J = 7.0 Hz, 1H), 1.54 (d, J = 7.0 Hz, 3H). |
| 84 | $^1H$ NMR (500 MHz, DMSO-$d_6$) δ 7.60-7.48 (m, 2H), 7.16-7.13 (m, 1H), 7.03 (dd, J = 7.5, 2.0 Hz, 1H), 6.78 (s, 2H), 4.63 (q, J = 7.0 Hz, 1H), 3.87 (s, 3H), 1.48 (d, J = 7.0 Hz, 3H). |
| 85 | $^1H$ NMR (500 MHz, DMSO-$d_6$) δ 7.43-7.32 (m, 3H), 7.23-7.21 (m, 1H), 6.77 (s, 2H), 4.71 (q, J = 7.0 Hz, 1H), 2.82-2.71 (m, 1H), 2.60-2.49 (m, 1H), 1.52 (d, J = 7.0 Hz, 3H), 1.20 (t, J = 8.0 Hz, 3H). |
| 86 | $^1H$ NMR (500 MHz, DMSO-$d_6$) δ 7.79-7.71 (m, 4H), 6.77 (s, 2H), 4.68 (q, J = 7.0 Hz, 1H), 1.54 (d, J = 7.0 Hz, 3H). |
| 87 | $^1H$ NMR (500 MHz, DMSO-$d_6$) δ 7.54-7.42 (m, 4H), 6.78 (s, 2H), 4.58 (q, J = 7.0 Hz, 1H), 1.56 (d, J = 7.0 Hz, 3H). |
| 88 | $^1H$ NMR (500 MHz, DMSO-$d_6$) δ 10.16 (s, 1H), 7.73-7.67 (m, 2H), 7.56-7.50 (m, 2H), 6.78 (s, 2H), 4.69 (q, J = 7.0 Hz, 1H), 4.48-4.76 (m, 1H), 3.79-3.77 (m, 1H), 2.07 (s, 3H), 1.52 (d, J = 7.0 Hz, 3H), 1.08 (t, J = 8.0 Hz, 3H). |
| 89 | $^1H$ NMR (500 MHz, DMSO-$d_6$) δ 7.49-7.42 (m, 2H), 7.39-7.33 (m, 2H), 6.77 (s, 2H), 4.79 (q, J = 7.0 Hz, 1H), 2.45 (s, 3H), 2.39 (s, 3H), 1.47 (d, J = 7.0 Hz, 3H). |
| 90 | $^1H$ NMR (500 MHz, DMSO-$d_6$) δ 7.22-7.16 (m, 2H), 6.77 (s, 2H), 6.70-6.64 (m, 2H), 4.56 (q, J = 7.0 Hz, 1H), 3.02 (s, 6H), 1.45 (d, J = 7.0 Hz, 3H). |
| 91 | $^1H$ NMR (500 MHz, DMSO-$d_6$) δ 7.29 (t, J = 7.5 Hz, 2H), 7.24-7.18 (m, 2H), 7.04-6.97 (m, 2H), 6.94-6.92 (m, 1H), 6.89-6.83 (m, 2H), 6.67 (s, 1H), 6.36 (s, 2H), 4.61 (q, J = 7.0 Hz, 1H), 2.19 (s, 3H), 1.42 (d, J = 6.5 Hz, 3H). |

TABLE 2-continued

| No. | $^1$H NMR data of compounds $^1$H NMR |
|---|---|
| 92 | $^1$H NMR (500 MHz, DMSO-$d_6$) δ 7.21-7.15(m, 2H), 7.03-6.96 (m, 2H), 6.78 (s, 2H), 6.51 (dd, J = 15.0, 1.0 Hz, 1H), 5.25-5.53 (m, 1H), 4.59 (q, J = 7.0 Hz, 1H), 4.47-4.45 (m, 1H), 3.85-3.83 (m, 1H), 1.76 (dd, J = 6.5, 1.0 Hz, 3H), 1.46 (d, J = 7.0 Hz, 3H), 1.36 (t, J = 8.0 Hz, 3H). |
| 93 | $^1$H NMR (500 MHz, DMSO-$d_6$) δ 7.38 (dd, J = 7.5, 2.0 Hz, 1H), 7.36-7.30 (m, 2H), 7.30-7.22 (m, 2H), 7.25-7.17 (m, 1H), 7.10-7.08(m, 1H), 6.81 (s, 2H), 6.73-6.71 (m, 1H), 6.67-6.64 (m, 1H), 5.38 (s, 2H), 4.83 (q, J = 7.0 Hz, 1H), 4.28-4.21 (m, 1H), 3.18-3.16 (m, 1H), 1.57 (d, J = 7.0 Hz, 3H). |
| 94 | $^1$H NMR (500 MHz, DMSO-$d_6$) δ 9.40 (s, 1H), 7.35-7.23 (m, 5H), 6.79 (s, 2H), 5.06 (q, J = 7.0 Hz, 1H), 4.46 (s, 2H), 1.60 (p, J = 7.0 Hz, 1H), 1.52 (d, J = 7.0 Hz, 3H), 0.45-0.40 (m, 2H), 0.25-0.20 (m, 2H). |
| 95 | $^1$H NMR (500 MHz, DMSO-$d_6$) δ 6.78 (s, 2H), 5.98-5.91 (m, 1H), 5.08-4.97 (m, 2H), 4.71 (q, J = 7.0 Hz, 1H), 2.80-2.79 (m, 2H), 1.41 (d, J = 7.0 Hz, 3H), 1.08 (p, J = 7.0 Hz, 1H), 0.20-0.16 (m, 2H), 0.11-0.01 (m, 2H). |
| 96 | $^1$H NMR (500 MHz, DMSO-$d_6$) δ 7.43-7.40 (m, 2H), 7.33-7.24 (m, 3H), 7.17-7.10 (m, 2H), 7.06-7.03 (m, 1H), 7.03-6.96 (m, 2H), 6.80 (s, 2H), 4.82 (q, J = 7.0 Hz, 1H), 1.60 (d, J = 7.0 Hz, 3H). |
| 97 | $^1$H NMR (500 MHz, DMSO-$d_6$) δ 7.39-7.36 (m, 2H), 7.31-7.24 (m, 3H), 6.79 (s, 2H), 4.54 (q, J = 7.0 Hz, 1H), 2.77-2.72 (m, 1H), 2.46-2.41 (m, 1H), 1.37 (d, J = 7.0 Hz, 3H), 1.16 (t, J = 6.0 Hz, 3H). |
| 98 | $^1$H NMR (500 MHz, DMSO-$d_6$) δ 8.21 (s, 1H), 7.66-7.58 (m, 2H), 7.57-7.51 (m, 3H), 6.77 (s, 2H), 4.74 (q, J = 7.0 Hz, 1H), 2.92-2.89 (m, 1H), 2.77-2.75 (m, 1H), 1.58-1.54 (m, 1H), 1.43 (d, J = 7.0 Hz, 3H), 1.03-1.00 (m, 1H), 0.86 (t, J = 6.0 Hz, 3H). |
| 99 | $^1$H NMR (500 MHz, DMSO-$d_6$) δ7.55-7.46 (m, 5H), 6.78 (s, 2H), 4.69 (q, J = 7.0 Hz, 1H), 2.88 (s, 6H), 1.48 (d, J = 7.0 Hz, 3H). |
| 100 | $^1$H NMR (500 MHz, DMSO-$d_6$) δ 9.40 (s, 1H), 7.22-7.16 (m, 2H), 7.13-7.11 (m, 2H), 6.78 (s, 2H), 4.66 (q, J = 7.0 Hz, 1H), 4.37-4.30 (m, 1H), 4.19-4.16 (m, 1H), 3.15-3.08 (m, 1H), 2.77-2.71 (m, 1H), 2.21 (s, 3H), 1.56 (d, J = 7.0 Hz, 3H), 0.87 (t, J = 8.0 Hz, 3H). |
| 101 | $^1$H NMR (500 MHz, DMSO-$d_6$) δ 9.40 (s, 1H), 7.57-7.53 (m, 5H), 7.35-7.23 (m, 5H), 6.79 (s, 2H), 4.84 (q, J = 7.0 Hz, 1H), 4.06-4.04 (m, 1H), 3.99-3.96 (m, 1H), 1.34 (d, J = 7.0 Hz, 3H). |
| 102 | $^1$H NMR (500 MHz, DMSO-$d_6$) δ 9.16 (s, 1H), 7.42-7.33 (m, 4H), 6.46 (s, 2H), 4.70 (q, J = 7.0 Hz, 1H), 4.24-4.19 (m, 2H), 2.34 (s, 3H), 1.43 (d, J = 7.0 Hz, 3H). |
| 103 | $^1$H NMR (500 MHz, DMSO-$d_6$) δ 9.40 (s, 1H), 7.28-7.22 (m, 2H), 6.93-6.87 (m, 2H), 6.79 (s, 2H), 4.58 (q, J = 7.0 Hz, 1H), 4.15-4.13 (m, 1H), 3.82-3.80 (m, 1H), 3.79 (s, 3H), 2.61 (s, 3H), 1.57 (d, J = 7.0 Hz, 3H). |
| 104 | $^1$H NMR (500 MHz, DMSO-$d_6$) δ 9.40 (s, 1H), 7.61-7.51 (m, 6H), 6.78 (s, 2H), 6.40-6.39 (m, 1H), 6.37-6.31 (m, 1H), 4.95-4.94 (m, 1H), 4.77 (q, J = 7.0 Hz, 1H), 4.28-4.26 (m, 1H), 1.56 (d, J = 7.0 Hz, 3H). |
| 105 | $^1$H NMR (500 MHz, DMSO-$d_6$) δ 8.21 (s, 1H), 7.61-7.50 (m, 5H), 7.30-7.21 (m, 4H), 7.21-7.17 (m, 1H), 6.80 (s, 2H), 4.67 (q, J = 7.0 Hz, 1H), 3.27-3.12 (m, 2H), 3.01-2.98 (m, 1H), 2.43-2.38 (m, 1H), 1.45 (d, J = 7.0 Hz, 3H). |
| 106 | $^1$H NMR (500 MHz, DMSO-$d_6$) δ 7.64-7.57 (m, 2H), 7.41-7.39 (m, 2H), 7.22-7.13 (m, 2H), 6.75 (s, 2H), 4.95 (dd, J = 10.0, 1.5 Hz, 1H), 4.76 (dd, J = 17, 1.5 Hz, 1H), 4.62 (q, J = 7.0 Hz, 1H), 3.57 (s, 3H), 1.50 (d, J = 7.0 Hz, 3H). |
| 107 | $^1$H NMR (500 MHz, DMSO-$d_6$) δ 7.57-7.51 (m, 3H), 7.41-7.27 (m, 7H), 6.83 (s, 2H), 5.15 (d, J = 12.5 Hz, 1H), 5.04 (d, J = 12.5 Hz, 1H), 4.52 (q, J = 7.0 Hz, 1H), 1.50 (d, J = 7.0 Hz, 3H). |
| 108 | $^1$H NMR (500 MHz, DMSO-$d_6$) δ 12.06 (s, 1H), 6.81 (s, 2H), 6.64 (dd, J = 7.5, 1.5 Hz, 1H), 6.17 (t, J = 7.5 Hz, 1H), 6.07 (dd, J = 7.5, 1.5 Hz, 1H), 5.48 (d, J = 12.5 Hz, 1H), 4.72 (d, J = 12.5 Hz, 1H), 4.47 (q, J = 7.0Hz, 1H), 2.72-2.65 (m, 1H), 2.43-2.36 (m, 1H), 1.58 (d, J = 7.0 Hz, 3H), 0.96 (t, J = 8.0 Hz, 3H). |
| 109 | $^1$H NMR (500 MHz, DMSO-$d_6$) δ8.07-7.96 (m, 4H), 7.85-7.83 (m, 1H), 7.66-7.57 (m, 2H), 6.22 (s, 2H), 4.70 (q, J = 7.0 Hz, 1H), 3.56 (s, 3H), 1.55 (d, J = 7.0 Hz, 3H). |
| 110 | $^1$H NMR (500 MHz, DMSO-$d_6$) δ 5.95 (s, 1H), 4.68 (q, J = 7.0 Hz, 1H), 2.70 (s, 3H), 2.43 (s, 3H), 2.40 (s, 3H), 1.49 (d, J = 7.0 Hz, 3H). |
| 111 | $^1$H NMR (500 MHz, DMSO-$d_6$) δ 6.12 (s, 1H), 4.57 (q, J = 7.0 Hz, 1H), 3.75-3.73 (m, 1H), 3.25-3.22 (m, 1H), 2.45 (s, 3H), 2.43 (s, 3H), 1.32 (d, J = 7.0 Hz, 3H), 1.26 (t, J = 8.0 Hz, 3H). |
| 112 | $^1$H NMR (500 MHz, DMSO-$d_6$) δ 9.94 (s, 1H), 4.65 (q, J = 7.0 Hz, 1H), 2.45 (s, 3H), 2.43 (s, 3H), 2.07 (s, 3H), 1.41 (d, J = 7.0 Hz, 3H). |
| 113 | $^1$H NMR (500 MHz, DMSO-$d_6$) δ 10.47 (s, 1H), 7.53-7.51 (m, 1H), 6.43-6.41 (m, 1H), 6.23-6.18 (m, 1H), 4.69 (q, J = 7.0 Hz, 1H), 3.87-3.85 (m, 1H), 3.74-3.72 (m, 1H), 2.47 (s, 3H), 2.47 (s, 3H), 1.50 (d, J = 6.5 Hz, 3H). |
| 114 | 1H NMR (500 MHz, DMSO-$d_6$) δ8.00-7.93 (m, 2H), 7.63-7.55 (m, 1H), 7.55-7.53 (m, 2H), 4.60 (q, J = 7.0 Hz, 1H), 2.45 (s, 3H), 2.43 (s, 3H), 1.56 (d, J = 7.0 Hz, 3H). |
| 115 | $^1$H NMR (500 MHz, DMSO-$d_6$) δ 7.39-7.29 (m, 4H), 7.28-7.25 (m, 1H), 6.22 (s, 1H), 4.93-4.89 (m, 1H), 4.65 (q, J = 7.0 Hz, 1H), 4.27-4.25 (m, 1H), 2.51 (s, 3H), 2.50 (s, 3H), 1.48 (d, J = 7.0 Hz, 3H). |
| 116 | $^1$H NMR (500 MHz, DMSO-$d_6$) δ 6.80 (s, 2H), 4.63 (q, J = 7.0 Hz, 1H), 2.75-2.67 (m, 2H), 1.82-1.79 (m, 2H), 1.71-1.63 (m, 2H), 1.49 (d, J = 7.0 Hz, 3H), 1.01-0.91 (m, 2H), 0.84-0.75 (m, 2H). |
| 117 | $^1$H NMR (500 MHz, DMSO-$d_6$) δ 6.80 (s, 2H), 4.68 (q, J = 7.0 Hz, 1H), 2.69-2.57(m, 2H), 2.45-2.37 (m, 2H), 1.47 (d, J = 6.5 Hz, 3H), 1.13-1.03(m, 2H), 0.74-0.66 (m, 2H). |
| 118 | $^1$H NMR (500 MHz, DMSO-$d_6$) 6.43-6.34 (m, 2H), 6.22 (s, 1H), 4.84 (d, J = 12.5 Hz, 1H), 4.70-4.62 (m, 2H), 2.45 (s, 3H), 2.43 (s, 3H), 1.51 (d, J = 7.0 Hz, 3H). |

Several methods for preparing the compounds of the present invention are detailedly illustrated in the following schemes and examples. The starting materials can be purchased commercially or can be prepared by methods known in the literature or according to the detailed illustrations. Those skilled in the art will appreciate that other synthetic routes can also be utilized to synthesize the compounds of the present invention. Although specific starting materials and conditions in the synthetic route have been described below, they can be easily replaced with other similar starting materials and conditions, and various isomers of compounds and the like produced by variations or variants of the preparation methods of the present invention are included in the scope of the present invention. Additionally, the preparation methods described below can be further modified in accordance with the present disclosure, using conventional chemical methods well known to those skilled in the art. For example, appropriate groups are protected during the reaction, and the like.

The method examples are provided below to facilitate a further understanding of the preparation method of the present invention, and the specific materials, types and conditions used are determined to be further description of the present invention and are not intended to limit its rational scope. The reagents used for synthesizing the following compounds indicated in the table below are either commercially available or can be readily prepared by those skilled in the art.

The examples of representative compounds are as follows, the synthetic methods of other compounds are similar, and will not be described in detail here.

1. Synthesis of Compound 3

Compound 3-1 (300 mg, 1.19 mmol), compound 3-2 (236 mg, 1.19 mmol), DCC (369 mg, 1.79 mmol) and dehydrated dichloromethane (20 ml) were added to a 50 ml round-bottom flask, reacted for 12 hours at room temperature. After completed reaction of the starting materials according to LC-MS detection, the reaction solution was concentrated, and separated by column chromatography to obtain compound 3 (180 mg, yield 35%).

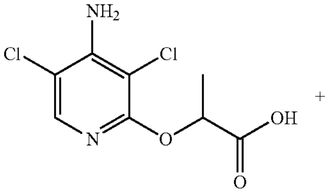

3-1

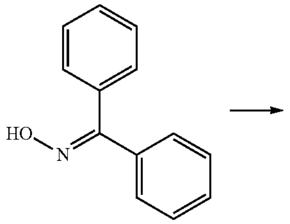

3-2

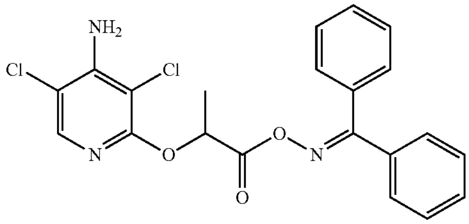

3

2. Synthesis of Compound 53

(1) Compound 53-1 (400 mg, 1.70 mmol), compound 53-2 (680 mg), a catalytic amount of TBAB (10 mg) and DMF (10 mL) were added to a 50 ml round-bottom flask, heated to 85° C. and reacted for 12 hours. After completed reaction of the starting materials according to LC-MS detection, the reaction solution was cooled to room temperature, and extracted with water (100 ml) and MTBE (50 ml×2). The organic phase was dried, concentrated, and separated by column chromatography to obtain compound 53-3 (360 mg, yield 47%).

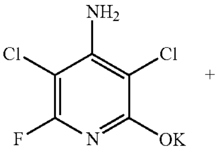

53-1

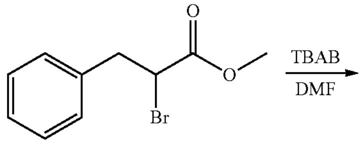

53-2

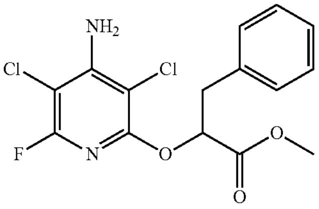

53-3

(2) Compound 53-3 (0.36 g, 1.17 mmol) and methanol (20 mg) were added to a 100 ml single mouth flask. Lithium hydroxide (48 mg, 2.0 mmol) was dissolved in 2 ml water and slowly added dropwise into the single mouth flask at room temperature. Agitated for 12 hours at room temperature. After completed reaction of the starting materials according to LC-MS detection, adjusted with 0.5M dilute hydrochloric acid to pH=5-6, concentrated and then extracted with water and ethyl acetate. The organic phase was dried and concentrated to obtain compound 53-4 (300 mg).

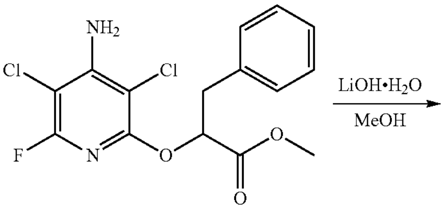

53-3

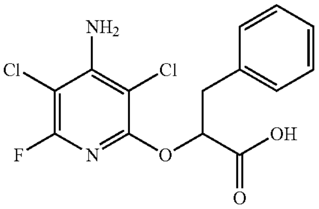

53-4

(3) Compound 53-4 (300 mg, 0.87 mmol), compound a (64 mg, 0.87 mmol), DCC (289 mg, 1.31 mmol) and dehydrated dichloromethane (20 ml) were added to a 50 ml round-bottom flask, reacted for 12 hours at room temperature. After completed reaction of the starting materials according to LC-MS detection, the reaction solution was concentrated, and separated by column chromatography to obtain compound 53 (110 mg, yield 32%).

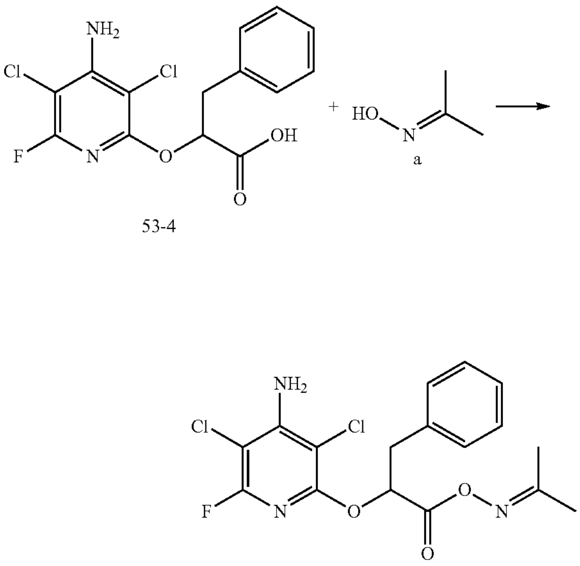

53-4 a 53

3. Synthesis of Compound 67

Compound b (400 mg, 1.49 mmol), compound a (109 mg, 1.49 mmol), DCC (459 mg, 2.24 mmol) and dehydrated DCM (20 ml) were added to a 100 ml round-bottom flask, reacted for 12 hours at room temperature. After completed reaction of the starting materials according to LC-MS detection, the reaction solution was concentrated, and separated by column chromatography to obtain compound 67 (150 mg, yield 31%), as a white solid.

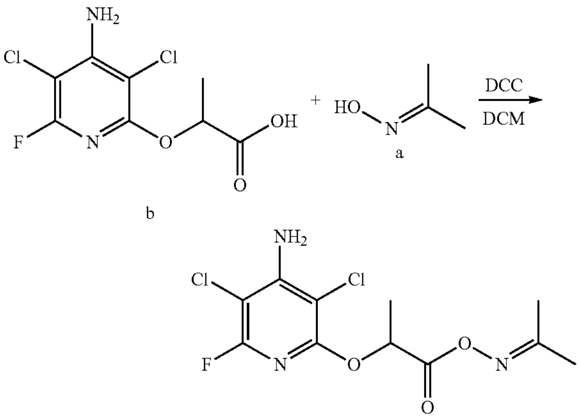

b a 67

4. Synthesis of Compound 113

(1) Compound 113-1 (500 mg, 1.77 mmol), potassium carbonate (488 mg, 3.53 mmol), 113-2 (427 mg, 2.65 mmol), a catalytic amount of DMAP (10 mg) and acetonitrile (20 ml) were added to a 50 ml round-bottom flask. Heated to 80° C. and reacted for 12 hours. After completed reaction of the starting materials according to LC-MS detection, the reaction solution was cooled to room temperature, concentrated, and separated by column chromatography to obtain compound 113-3 (400 mg, yield 62%), as a colorless oil.

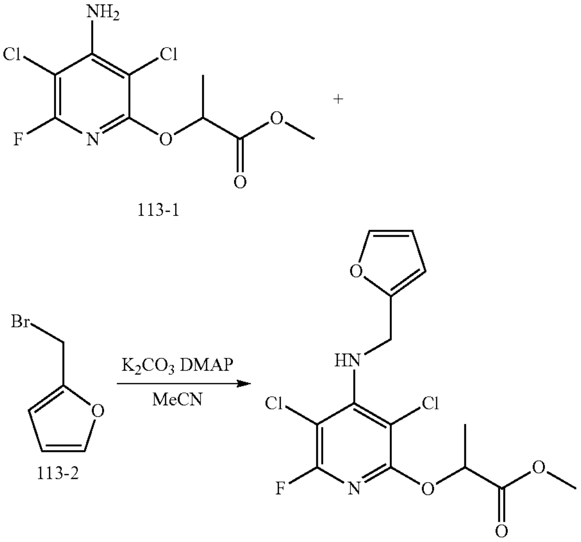

113-1 113-2 113-3

(2) Compound 113-3 (400 mg, 1.10 mmol) was dissolved in 20 mL methanol. LiOH solution (46.2 mg, 1.10 mmol) was dissolved in 5 ml water and slowly added dropwise into the reaction flask, reacted for 12 hours at room temperature. After completed reaction of the starting materials according to LC-MS detection, adjusted with 0.5M dilute hydrochloric acid to neutral, concentrated to remove methanol and then washed with ethyl acetate (10 mL×3) and water (100 mL). The organic phase was dried and concentrated to obtain compound 113-4 (300 mg, yield 78%).

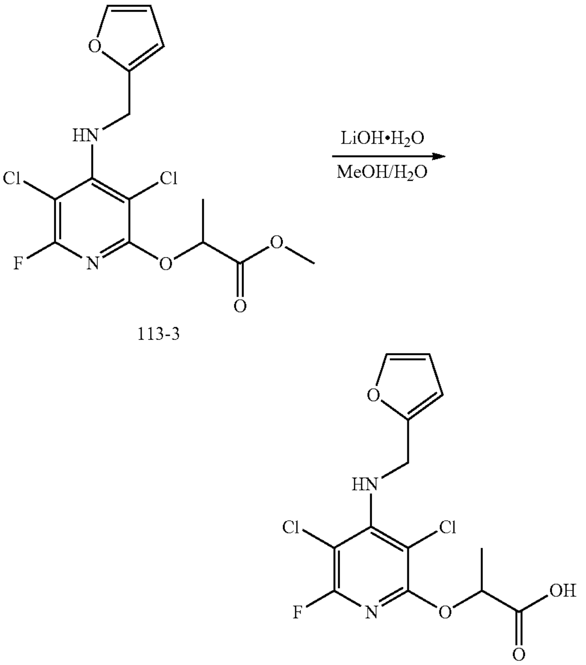

113-3 113-4

(3) Compound 113-4 (300 mg, 0.86 mmol), compound a (63 mg, 0.86 mmol), DCC (291 mg, 1.29 mmol) and dehydrated DCM (20 ml) were added to a 50 ml round-bottom flask, reacted for 12 hours at room temperature. After completed reaction of the starting materials according to LC-MS detection, the reaction solution was concentrated, and separated by column chromatography to obtain compound 113 (100 mg, yield 29%).

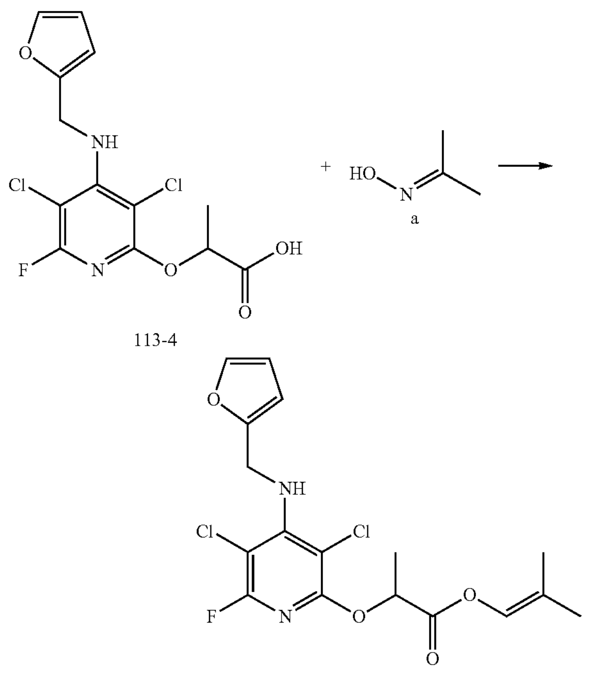

113-4

113

Biological Activity Evaluation:

The activity level standard of plants destruction (i. e. growth inhibition rate) is as follows:

Level 5: the growth inhibition rate is greater than 85%;

Level 4: the growth inhibition rate is equal to or greater than 60% and less than 85%;

Level 3: the growth inhibition rate is equal to or greater than 40% and less than 60%;

Level 2: the growth inhibition rate is equal to or greater than 20% and less than 40%;

Level 1: the growth inhibition rate is equal to or greater than 5% and less than 20%;

Level 0: the growth inhibition rate is less than 5%;

The above described growth inhibition rate is fresh weight inhibition rate.

Post-emergence test experiment: Monocotyledonous and dicotyledonous weed seeds and main crop seeds (i. e. wheat, corn, rice, soybean, cotton, oilseed, millet and sorghum.) were put into a plastic pot loaded with soil. Then covered with 0.5-2 cm soil, the seeds were allowed to grow in good greenhouse environment. The test plants were treated at 2-3 leaf stage 2 weeks after sowing. The test compounds of the invention were dissolved with acetone respectively, then added with tween-80, and using 1.5 liters per hectare of an emulsible concentrate of methyl oleate as a synergist, and diluted by certain amount of water to certain concentration. The solution was sprayed to the plants with a sprayer. Then the plants were cultured for 3 weeks in the greenhouse, and the experiment result of weed controlling effect was listed in tables 3-4.

TABLE 3

Activity test results of compounds (1000 g a.i./ha)

| No. | *Digitaria sanguinalis* | *Echinochloa crusgalli* | *Setaria viridis* | *Leptochloa chinensis* | *Monochoria Vaginalis* | *Galium spurium* | *Murdannia triquetra* |
|---|---|---|---|---|---|---|---|
| 1 | 5 | 5 | 5 | 5 | 5 | 5 | 5 |
| 2 | 5 | 5 | 5 | 5 | 5 | 5 | 5 |
| 3 | 5 | 5 | 5 | 5 | 5 | 5 | 5 |
| 4 | 5 | 5 | 5 | 5 | 5 | 5 | 5 |
| 5 | 5 | 5 | 5 | 5 | 5 | 5 | 5 |
| 6 | 5 | 5 | 5 | 5 | 5 | 5 | 5 |
| 7 | 5 | 5 | 5 | 5 | 5 | 5 | 5 |
| 8 | 5 | 5 | 5 | 5 | 5 | 5 | 5 |
| 9 | 5 | 5 | 5 | 5 | 5 | 5 | 5 |
| 10 | 5 | 5 | 5 | 5 | 5 | 5 | 5 |
| 11 | 5 | 5 | 5 | 5 | 5 | 5 | 5 |
| 12 | 5 | 5 | 5 | 5 | 5 | 5 | 5 |
| 13 | 5 | 5 | 5 | 5 | 5 | 5 | 5 |
| 14 | 5 | 5 | 5 | 5 | 5 | 5 | 5 |
| 15 | 5 | 5 | 5 | 5 | 5 | 5 | 5 |
| 16 | 5 | 5 | 5 | 5 | 5 | 5 | 5 |
| 17 | 5 | 5 | 5 | 5 | 5 | 5 | 5 |
| 18 | 5 | 5 | 5 | 5 | 5 | 5 | 5 |
| 19 | 5 | 5 | 5 | 5 | 5 | 5 | 5 |
| 20 | 5 | 5 | 5 | 5 | 5 | 5 | 5 |
| 21 | 5 | 5 | 5 | 5 | 5 | 5 | 5 |
| 22 | 5 | 5 | 5 | 5 | 5 | 5 | 5 |
| 23 | 5 | 5 | 5 | 5 | 5 | 5 | 5 |
| 24 | 5 | 5 | 5 | 5 | 5 | 5 | 5 |
| 25 | | | | | 5 | 5 | 5 |
| 26 | | | | | 5 | 5 | 5 |
| 27 | | | | | 5 | 5 | 5 |
| 28 | | | | | 5 | 5 | 5 |
| 29 | | | | | 5 | 5 | 5 |
| 30 | | | | | 5 | 5 | 5 |

TABLE 3-continued

| Activity test results of compounds (1000 g a.i./ha) | | | | | | | |
|---|---|---|---|---|---|---|---|
| No. | *Digitaria sanguinalis* | *Echinochloa crusgalli* | *Setaria viridis* | *Leptochloa chinensis* | *Monochoria Vaginalis* | *Galium spurium* | *Murdannia triquetra* |
| 31 | | | | | 5 | 5 | 5 |
| 32 | | | | | 5 | 5 | 5 |
| 33 | | | | | 5 | 5 | 5 |
| 34 | | | | | 5 | 5 | 5 |
| 35 | | | | | 5 | 5 | 5 |
| 36 | | | | | 5 | 5 | 5 |
| 37 | | | | | 5 | 5 | 5 |
| 38 | | | | | 5 | 5 | 5 |
| 39 | | | | | 5 | 5 | 5 |
| 40 | | | | | 5 | 5 | 5 |
| 41 | | | | | 5 | 5 | 5 |
| 42 | | | | | 5 | 5 | 5 |
| 43 | | | | | 5 | 5 | 5 |
| 44 | | | | | 5 | 5 | 5 |
| 45 | | | | | 5 | 5 | 5 |
| 46 | | | | | 5 | 5 | 5 |
| 47 | | | | | 5 | 5 | 5 |
| 48 | | | | | 5 | 5 | 5 |
| 49 | | | | | 5 | 5 | 5 |
| 50 | | | | | 5 | 5 | 5 |
| 51 | | | | | 5 | 5 | 5 |
| 52 | | | | | 5 | 5 | 5 |
| 53 | | | | | 5 | 5 | 5 |
| 54 | | | | | 5 | 5 | 5 |
| 55 | | | | | 5 | 5 | 5 |
| 56 | | | | | 5 | 5 | 5 |
| 57 | | | | | 5 | 5 | 5 |
| 58 | | | | | 5 | 5 | 5 |
| 59 | | | | | 5 | 5 | 5 |
| 60 | | | | | 5 | 5 | 5 |
| 61 | | | | | 5 | 5 | 5 |
| 62 | | | | | 5 | 5 | 5 |
| 63 | | | | | 5 | 5 | 5 |
| 64 | | | | | 5 | 5 | 5 |
| 65 | | | | | 5 | 5 | 5 |
| 66 | | | | | 5 | 5 | 5 |
| 67 | 5 | 5 | 5 | 5 | 5 | 5 | 5 |
| 68 | 5 | 5 | 5 | 5 | 5 | 5 | 5 |
| 69 | 5 | 5 | 5 | 5 | 5 | 5 | 5 |
| 70 | 5 | 5 | 5 | 5 | 5 | 5 | 5 |
| 71 | 5 | 5 | 5 | 5 | 5 | 5 | 5 |
| 72 | 5 | 5 | 5 | 5 | 5 | 5 | 5 |
| 73 | 5 | 5 | 5 | 5 | 5 | 5 | 5 |
| 74 | 5 | 5 | 5 | 5 | 5 | 5 | 5 |
| 75 | 5 | 5 | 5 | 5 | 5 | 5 | 5 |
| 76 | 5 | 5 | 5 | 5 | 5 | 5 | 5 |
| 77 | 5 | 5 | 5 | 5 | 5 | 5 | 5 |
| 78 | 5 | 5 | 5 | 5 | 5 | 5 | 5 |
| 79 | 5 | 5 | 5 | 5 | 5 | 5 | 5 |
| 80 | 5 | 5 | 5 | 5 | 5 | 5 | 5 |
| 81 | 5 | 5 | 5 | 5 | 5 | 5 | 5 |
| 82 | 5 | 5 | 5 | 5 | 5 | 5 | 5 |
| 83 | 5 | 5 | 5 | 5 | 5 | 5 | 5 |
| 84 | 5 | 5 | 5 | 5 | 5 | 5 | 5 |
| 85 | 5 | 5 | 5 | 5 | 5 | 5 | 5 |
| 86 | 5 | 5 | 5 | 5 | 5 | 5 | 5 |
| 87 | 5 | 5 | 5 | 5 | 5 | 5 | 5 |
| 88 | 5 | 5 | 5 | 5 | 5 | 5 | 5 |
| 89 | 5 | 5 | 5 | 5 | 5 | 5 | 5 |
| 90 | 5 | 5 | 5 | 5 | 5 | 5 | 5 |
| 91 | 5 | 5 | 5 | 5 | 5 | 5 | 5 |
| 92 | 5 | 5 | 5 | 5 | 5 | 5 | 5 |
| 93 | 5 | 5 | 5 | 5 | 5 | 5 | 5 |
| 94 | 5 | 5 | 5 | 5 | 5 | 5 | 5 |
| 95 | 5 | 5 | 5 | 5 | 5 | 5 | 5 |
| 96 | 5 | 5 | 5 | 5 | 5 | 5 | 5 |
| 97 | 5 | 5 | 5 | 5 | 5 | 5 | 5 |
| 98 | 5 | 5 | 5 | 5 | 5 | 5 | 5 |
| 99 | 5 | 5 | 5 | 5 | 5 | 5 | 5 |
| 100 | 5 | 5 | 5 | 5 | 5 | 5 | 5 |
| 101 | 5 | 5 | 5 | 5 | 5 | 5 | 5 |
| 102 | 5 | 5 | 5 | 5 | 5 | 5 | 5 |
| 103 | 5 | 5 | 5 | 5 | 5 | 5 | 5 |
| 104 | 5 | 5 | 5 | 5 | 5 | 5 | 5 |
| 105 | 5 | 5 | 5 | 5 | 5 | 5 | 5 |

TABLE 3-continued

Activity test results of compounds (1000 g a.i./ha)

| No. | *Digitaria sanguinalis* | *Echinochloa crusgalli* | *Setaria viridis* | *Leptochloa chinensis* | *Monochoria Vaginalis* | *Galium spurium* | *Murdannia triquetra* |
|---|---|---|---|---|---|---|---|
| 106 | 5 | 5 | 5 | 5 | 5 | 5 | 5 |
| 107 | 5 | 5 | 5 | 5 | 5 | 5 | 5 |
| 108 | 5 | 5 | 5 | 5 | 5 | 5 | 5 |
| 109 | 5 | 5 | 5 | 5 | 5 | 5 | 5 |
| 110 | 5 | 5 | 5 | 5 | 5 | 5 | 5 |
| 111 | 5 | 5 | 5 | 5 | 5 | 5 | 5 |
| 112 | 5 | 5 | 5 | 5 | 5 | 5 | 5 |
| 113 | 5 | 5 | 5 | 5 | 5 | 5 | 5 |
| 114 | 5 | 5 | 5 | 5 | 5 | 5 | 5 |
| 115 | 5 | 5 | 5 | 5 | 5 | 5 | 5 |
| 116 | 5 | 5 | 5 | 5 | 5 | 5 | 5 |
| 117 | 5 | 5 | 5 | 5 | 5 | 5 | 5 |
| 118 | 5 | 5 | 5 | 5 | 5 | 5 | 5 |

TABLE 4

Test results of post-emergence weeds

| No. | Japonica rice | Indica rice | *Cyperus iria* |
|---|---|---|---|
| 4 | 0 | 0 | 5 |
| 12 | 0 | 0 | 5 |
| 67 | 0 | 0 | 5 |
| 68 | 0 | 0 | 5 |
| 69 | 0 | 0 | 5 |
| 70 | 0 | 0 | 5 |
| 75 | 0 | 0 | 5 |
| 84 | 0 | 0 | 5 |
| 87 | 0 | 0 | 5 |
| 88 | 0 | 0 | 5 |
| 90 | 0 | 0 | 5 |
| 92 | 0 | 0 | 5 |
| 100 | 0 | 0 | 5 |
| 104 | 0 | 0 | 5 |
| 117 | 0 | 0 | 5 |
| Control compound A (600 g a.i./ha) | 3 | 3 | 5 |
| Control compound A (300 g a.i./ha) | 2 | 3 | 4 |

Note:
the application dose was active ingredient 600 g/ha, plus water 450 kg/ha.

Control Compound A:

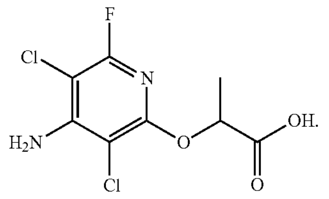 [SMILES: CC(Oc1nc(F)c(Cl)c(N)c1Cl)C(=O)O]

It is observed from the testing that the compounds of the present invention have excellent selectivity to rice, regardless of *japonica* or *indica* rice, whereas the control compound has great inhibition to rice which results to decrease of biomass and swelling of root thus not available for commercial production. As observed, the present invention has unexpected high efficacy.

Experiment on Weed Effect in Pre-Emergence Stage

Seeds of monocotyledonous and dicotyledonous weeds and main crops (e. g. wheat, corn, rice, soybean, cotton, oilseed, millet and sorghum) were put into a plastic pot loaded with soil and covered with 0.5-2 cm soil. The test compounds of the present invention was dissolved with acetone, then added with tween-80, diluted by a certain amount of water to reach a certain concentration, and sprayed immediately after sowing. The obtained seeds were incubated for 4 weeks in the greenhouse after spraying and the test results were observed. It was observed that the herbicide mostly had excellent effect at the application rate of 250 g a.i./ha, especially to weeds such as *Echinochloa crusgalli, Digitaria sanguinalis* and *Abutilon theophrasti*, etc. Many compounds had good selectivity for corn, wheat, rice, soybean, oilseed rape, etc.

Through experiments, we found that the compounds of the present invention generally had better weed control effects, especially for major gramineous weeds such as *Echinochloa crusgalli, Digitaria sanguinalis*, and *Setaria viridis*, which are widely occurring in corn fields, rice fields and wheat fields, and major broad-leaved weeds such as *Abutilon theophrasti, Rorippa indica* and *Bidens pilosa*, and had excellent commercial value. In particular, we noticed that they had extremely high activity against broad-leaved weeds, such as *Rorippa indica, Descurainia sophia, Capsella bursa-pastoris, Lithospermum arvense, Galium spurium* and *Stellaria media*, which were resistant to ALS inhibitors.

Transplanted rice safety evaluation and weed control effect evaluation in rice field: Rice field soil was loaded into a 1/1,000,000 ha pot. The seeds of *Scirpus* juncoides, *Sagittaria trifolia* and *Monochoria vaginalis* were sowed and gently covered with soil, then left to stand still in greenhouse in the state of 0.5-1 cm of water storage. The tuber of *Sagittaria trifolia* was planted in the next day or 2 days later. It was kept at 3-4 cm of water storage thereafter. The weeds were treated by dripping the WP or SC water diluents prepared according to the common preparation method of the compounds of the present invention with pipette homogeneously to achieve specified effective amount when *Scirpus* juncoides, and *Monochoria vaginalis* reached 0.5 leaf stage and *Sagittaria trifolia* reached the time point of primary leaf stage.

In addition, the rice field soil that loaded into the 1/1,000,000 ha pot was leveled to keep water storage at 3-4 cm depth. The 3 leaf stage rice (*japonica* rice) was transplanted at 3 cm of transplanting depth the next day. The compound of the present invention was treated by the same way after 5 days of transplantation.

The fertility condition of *Scirpus* juncoides, *Sagittaria trifolia* and *Monochoria vaginalis* 14 days after the treatment of the compound of the invention and the fertility condition of rice 21 days after the treatment of the compound of the invention respectively with the naked eye. Evaluate the weed control effect with 0-5 activity standard level. Many compounds show excellent activity and selectivity.

TABLE 5

| Test results of activity and safety (1000 g a.i./ha) | | | | |
|---|---|---|---|---|
| No. | Rice | *Monochoria Vaginalis* | *Scirpus juncoides* | *Sagittaria trifolia* |
| 1 | 0 | 5 | 4 | 4 |
| 2 | 0 | 5 | 4 | 4 |
| 3 | 0 | 5 | 4 | 5 |
| 4 | 0 | 5 | 4 | 5 |
| 70 | 0 | 5 | 4 | 4 |
| 84 | 0 | 5 | 4 | 4 |
| 88 | 0 | 5 | 4 | 4 |

Note:
The seeds of *Scirpus juncoides*, *Sagittaria trifolia* and *Monochoria vaginalis* were collected from Heilongjing Province of China. Tests indicated that the weeds were resistant to common rate of pyrazosulfuron-ethyl and penoxsulam.

It can be seen from the experiments that the compounds of the present invention had excellent activity against weeds having an anti-ALS inhibiting activity which cause a serious challenge in production, and can solve the increasingly serious problem of resistance.

At the same time, it is found after several tests that the compound and the composition of the present invention have good selectivity to many gramineae weeds such as *Zoysia japonica, Cynodon dactylon, Festuca elata, Poa annua, Lolium perenne* and *Paspalum vaginatum* etc, and is able to control many important gramineous weeds and broad-leaved weeds. The compound also shows excellent selectivity and commercial value in the tests on wheat, corn, rice, sugarcane, soybean, cotton, oil sunflower, potato, orchards and vegetables in different herbicide application methods.

The invention claimed is:

1. A pyridyloxy carboxylic oxime derivative compound represented by formula I,

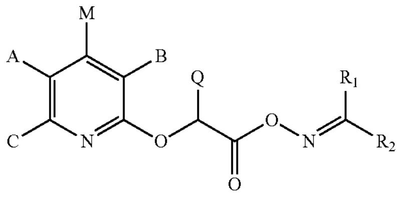

I wherein the compound represented by formula I is selected from:

| No. | A | B | C | Q |
|---|---|---|---|---|
| 1 | F | F | F | $CH_3$ |
| 2 | Cl | Cl | Cl | $CH_3$ |
| 3 | Cl | Cl | H | $CH_3$ |
| 4 | Cl | Cl | F | $CH_3$ |
| 5 | Cl | Cl | $CH_3$ | $CH_3$ |
| 6 | Cl | Cl | $CF_3$ | $CH_3$ |
| 7 | $CH_3$ | $CH_3$ | F | $CH_3$ |
| 8 | Et | Et | $CF_3$ | $CH_3$ |
| 9 | 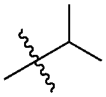 [SMILES: *C(C)C] | Cl | H | $CH_3$ |
| 10 | 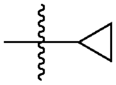 [SMILES: *C1CC1] | Cl | Cl | $CH_3$ |
| 11 | F | 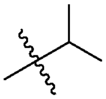 [SMILES: *C(C)C] | $CF_3$ | $CH_3$ |
| 12 | Br | Br | F | $CH_3$ |
| 13 | I | I | H | $CH_3$ |
| 14 | 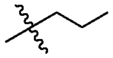 | 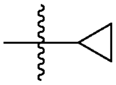 [SMILES: *C1CC1] | F | $CH_3$ |
| 15 | $CF_3$ | Cl | F | $CH_3$ |
| 16 | Cl | $CF_3$ | H | $CH_3$ |
| 17 | Cl | Cl | I | $CH_3$ |
| 18 | Cl | 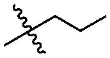 [SMILES: *CCC] | Br | $CH_3$ |
| 19 | $CH_3$ | $CH_3$ | $CH_3$ | $CH_3$ |
| 20 | Cl | $CH_3$ | F | $CH_3$ |
| 21 | Cl | $CH_3$ | H | $CH_3$ |
| 22 | Cl | 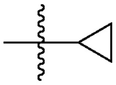 | F | $CH_3$ |
| 23 | Cl | Cl | H | $CH_3$ |
| 24 | Cl | Cl | Cl | $CH_3$ |
| 25 | Cl | Cl | F | Et |
| 26 | Cl | Cl | F | 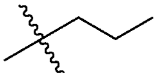 |
| 27 | Cl | Cl | F | 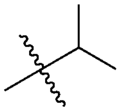 [SMILES: *C(C)C] |
| 28 | Cl | Cl | F | 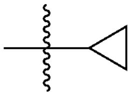 [SMILES: *C1CC1] |
| 29 | Cl | Cl | F | 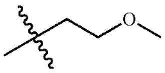 [SMILES: *CCOC] |
| 30 | Cl | Cl | F | 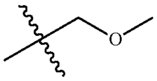 [SMILES: *COC] |
| 31 | Cl | Cl | F | 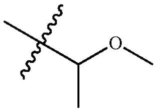 [SMILES: *C(C)OC] |
| 32 | Cl | Cl | F | 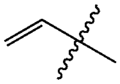 |

-continued

-continued
| | | | | |
|---|---|---|---|---|
| 33 | Cl | Cl | F | 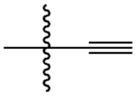 |
| 34 | Cl | Cl | F | F |
| 35 | Cl | Cl | F | Cl |
| 36 | Cl | Cl | F | Br |
| 37 | Cl | Cl | F | 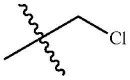 [SMILES: *CCl] |
| 38 | Cl | Cl | F | 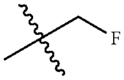 [SMILES: *CF] |
| 39 | Cl | Cl | F | 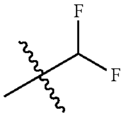 [SMILES: *C(F)F] |
| 40 | Cl | Cl | F | 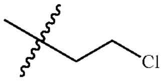 [SMILES: *CCCl] |
| 41 | Cl | Cl | F | $CF_3$ |
| 42 | Cl | Cl | F | 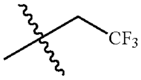 [SMILES: *CC(F)(F)F] |
| 43 | Cl | Cl | F | CN |
| 44 | Cl | Cl | F | 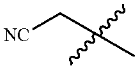 [SMILES: *CC#N] |
| 45 | Cl | Cl | F | $NH_2$ |
| 46 | Cl | Cl | F | 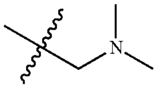 [SMILES: *CN(C)C] |
| 47 | Cl | Cl | F | 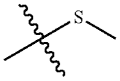 |
| 48 | Cl | Cl | F | 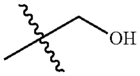 [SMILES: *CO] |
| 49 | Cl | Cl | F | $NO_2$ |
| 50 | Cl | Cl | F | 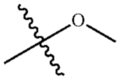 [SMILES: *OC] |
| 51 | Cl | Cl | F | 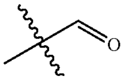 [SMILES: *C=O] |
| 52 | Cl | Cl | F | 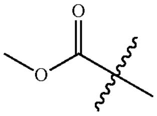 [SMILES: *C(=O)OC] |
| 53 | Cl | Cl | F | 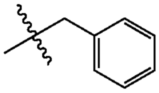 [SMILES: *Cc1ccccc1] |
| 54 | Cl | Cl | F | 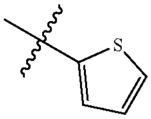 [SMILES: *c1cccs1] |
| 55 | Cl | Cl | F | 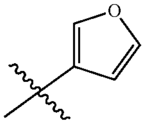 [SMILES: *c1ccoc1] |
| 56 | Cl | Cl | F | 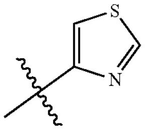 [SMILES: *c1cscn1] |
| 57 | Cl | Cl | F | 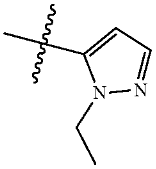 [SMILES: *c1ccnn1CC] |
| 58 | Cl | Cl | F | 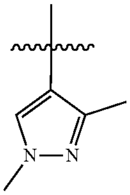 |
| 59 | Cl | Cl | F | 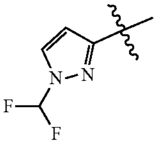 [SMILES: *c1ccn(C(F)F)n1] |
| 60 | Cl | Cl | F | 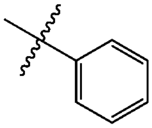 [SMILES: *c1ccccc1] |
| 61 | Cl | Cl | F | 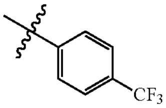 |
| 62 | Cl | Cl | F | 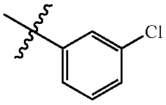 [SMILES: *c1cccc(Cl)c1] |
| 63 | Cl | Cl | F | 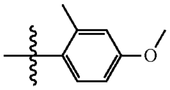 [SMILES: *c1ccc(OC)cc1C] |

-continued

| | | | | |
|---|---|---|---|---|
| 64 | Cl | Cl | F | 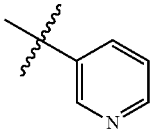 [SMILES: *c1cccnc1] |
| 65 | Cl | Cl | F | 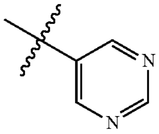 [SMILES: *c1cncnc1] |
| 66 | Cl | Cl | F | 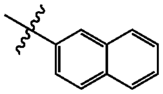 [SMILES: *c1ccc2ccccc2c1] |
| 67 | Cl | Cl | F | $CH_3$ |
| 68 | Cl | Cl | F | $CH_3$ |
| 69 | Cl | Cl | F | $CH_3$ |
| 70 | Cl | Cl | F | $CH_3$ |
| 71 | Cl | Cl | F | $CH_3$ |
| 72 | Cl | Cl | F | $CH_3$ |
| 73 | Cl | Cl | F | $CH_3$ |
| 74 | Cl | Cl | F | $CH_3$ |
| 75 | Cl | Cl | F | $CH_3$ |
| 76 | Cl | Cl | F | $CH_3$ |
| 77 | Cl | Cl | F | $CH_3$ |
| 78 | Cl | Cl | F | $CH_3$ |
| 79 | Cl | Cl | F | $CH_3$ |
| 80 | Cl | Cl | F | $CH_3$ |
| 81 | Cl | Cl | F | $CH_3$ |
| 82 | Cl | Cl | F | $CH_3$ |
| 83 | Cl | Cl | F | $CH_3$ |
| 84 | Cl | Cl | F | $CH_3$ |
| 85 | Cl | Cl | F | $CH_3$ |
| 86 | Cl | Cl | F | $CH_3$ |
| 87 | Cl | Cl | F | $CH_3$ |
| 88 | Cl | Cl | F | $CH_3$ |
| 89 | Cl | Cl | F | $CH_3$ |
| 90 | Cl | Cl | F | $CH_3$ |
| 91 | Cl | Cl | F | $CH_3$ |
| 92 | Cl | Cl | F | $CH_3$ |
| 93 | Cl | Cl | F | $CH_3$ |
| 94 | Cl | Cl | F | $CH_3$ |
| 95 | Cl | Cl | F | $CH_3$ |
| 96 | Cl | Cl | F | $CH_3$ |
| 97 | Cl | Cl | F | $CH_3$ |
| 98 | Cl | Cl | F | $CH_3$ |
| 99 | Cl | Cl | F | $CH_3$ |
| 100 | Cl | Cl | F | $CH_3$ |
| 101 | Cl | Cl | F | $CH_3$ |
| 102 | Cl | Cl | F | $CH_3$ |
| 103 | Cl | Cl | F | $CH_3$ |
| 104 | Cl | Cl | F | $CH_3$ |
| 105 | Cl | Cl | F | $CH_3$ |
| 106 | Cl | Cl | F | $CH_3$ |
| 107 | Cl | Cl | F | $CH_3$ |
| 108 | Cl | Cl | F | $CH_3$ |
| 109 | Cl | Cl | F | $CH_3$ |
| 110 | Cl | Cl | F | $CH_3$ |
| 111 | Cl | Cl | F | $CH_3$ |
| 112 | Cl | Cl | F | $CH_3$ |
| 113 | Cl | Cl | F | $CH_3$ |
| 114 | Cl | Cl | F | $CH_3$ |
| 115 | Cl | Cl | F | $CH_3$ |
| 116 | Cl | Cl | F | $CH_3$ |
| 117 | Cl | Cl | F | $CH_3$ |
| 118 | Cl | Cl | F | $CH_3$ |

| No. | $R_1$ | $R_2$ | M |
|---|---|---|---|
| 1 | Me | Me | $NH_2$ |
| 2 | Me | Ph | $NH_2$ |
| 3 | Ph | Ph | $NH_2$ |
| 4 | Me | Ph | $NH_2$ |
| 5 | Me | Ph | $NH_2$ |
| 6 | Me | Ph | $NH_2$ |
| 7 | Me | Ph | $NH_2$ |
| 8 | Me | Ph | $NH_2$ |
| 9 | Ph | Ph | $NH_2$ |
| 10 | Me | Ph | $NH_2$ |
| 11 | Me | Ph | $NH_2$ |
| 12 | Me | Ph | $NH_2$ |
| 13 | Ph | Ph | $NH_2$ |
| 14 | Me | Ph | $NH_2$ |
| 15 | Me | Me | $NH_2$ |
| 16 | Me | Me | $NH_2$ |
| 17 | Me | $—CH(CH_3)_2$ | $NH_2$ |
| 18 | Ph | Ph | $NH_2$ |
| 19 | Me | $CH_2CH_2Cl$ | $NH_2$ |
| 20 | Me | Me | $NH_2$ |
| 21 | Me | Me | $NH_2$ |
| 22 | Me | Me | $NH_2$ |
| 23 | Me | Me | $NH_2$ |
| 24 | Me | Me | $NH_2$ |
| 25 | Me | Ph | $NH_2$ |
| 26 | Me | Ph | $NH_2$ |
| 27 | Me | Et | $NH_2$ |
| 28 | Me | $—CH_2CH_2CH_3$ | $NH_2$ |
| 29 | Ph | Ph | $NH_2$ |
| 30 | Me | Ph | $NH_2$ |
| 31 | Me | $—C(CH_3)_3$ | $NH_2$ |
| 32 | Me | Me | $NH_2$ |
| 33 | Me | Me | $NH_2$ |
| 34 | Me | Me | $NH_2$ |
| 35 | Me | Me | $NH_2$ |
| 36 | Me | Me | $NH_2$ |
| 37 | Me | Me | $NH_2$ |
| 38 | Me | Me | $NH_2$ |
| 39 | Me | Me | $NH_2$ |
| 40 | Me | Me | $NH_2$ |
| 41 | Me | Me | $NH_2$ |
| 42 | Me | Me | $NH_2$ |
| 43 | Me | Me | $NH_2$ |
| 44 | Me | Me | $NH_2$ |
| 45 | Me | Me | $NH_2$ |
| 46 | Me | Me | $NH_2$ |
| 47 | Me | Me | $NH_2$ |
| 48 | Me | Me | $NH_2$ |
| 49 | Me | Me | $NH_2$ |
| 50 | Me | Me | $NH_2$ |
| 51 | Me | Me | $NH_2$ |
| 52 | Me | Me | $NH_2$ |
| 53 | Me | Me | $NH_2$ |
| 54 | Me | Me | $NH_2$ |
| 55 | Me | Me | $NH_2$ |
| 56 | Me | Me | $NH_2$ |
| 57 | Me | Me | $NH_2$ |
| 58 | Me | Me | $NH_2$ |
| 59 | Me | Me | $NH_2$ |
| 60 | Me | Ph | $NH_2$ |
| 61 | Me | OEt | $NH_2$ |
| 62 | H | H | $NH_2$ |
| 63 | H | Et | $NH_2$ |
| 64 | Me | Me | $NH_2$ |
| 65 | Me | Me | $NH_2$ |
| 66 | Et | Et | $NH_2$ |
| 67 | Me | Me | $NH_2$ |
| 68 | Et | $—CH(CH_3)_2$ | $NH_2$ |
| 69 | Et | n-Bu | $NH_2$ |
| 70 | Me | 4-Cl, Ph | $NH_2$ |
| 71 | Me | 4-$NO_2$, Ph | $NH_2$ |
| 72 | H | Ph | $NH_2$ |
| 73 | H | 3-$NO_2$, Ph | $NH_2$ |
| 74 | Et | Ph | $NH_2$ |
| 75 | $CH_2CH_2CH_3$ | Cl | $NH_2$ |
| 76 | n-Bu | OEt | $NH_2$ |
| 77 | Ph | 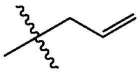 [SMILES: *CC=C] | $NH_2$ |

-continued

| | | | |
|---|---|---|---|
| 78 | Ph | Ph | $NH_2$ |
| 79 | Ph | 3-Cl, Ph | $NH_2$ |
| 80 | Ph | 4-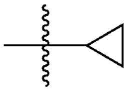 [SMILES: *C1CC1], Ph | $NH_2$ |
| 81 | 4-$CF_3$, Ph | Ph | $NH_2$ |
| 82 | 3-F, Ph | 4-Cl, Ph | $NH_2$ |
| 83 | 4-F, Ph | Ph | $NH_2$ |
| 84 | F | 2-OMe, Ph | $NH_2$ |
| 85 | Cl | 3-Et, Ph | $NH_2$ |
| 86 | Br | 4-CN, Ph | $NH_2$ |
| 87 | CN | 4-Cl, Ph | $NH_2$ |
| 88 | OEt | 4-NHCOMe, Ph | $NH_2$ |
| 89 | SMe | 4-SMe, Ph | $NH_2$ |
| 90 | $NO_2$ | 4-N(Me)$_2$, Ph | $NH_2$ |
| 91 | Ac | 4-NHOPh, Ph | $NH_2$ |
| 92 | COOEt | 4-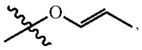, Ph | $NH_2$ |
| 93 | Bn | 2-$NH_2$, Ph | $NH_2$ |
| 94 | 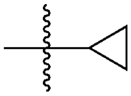 | CONHBn | $NH_2$ |
| 95 | 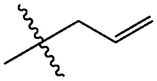 [SMILES: *CC=C] | 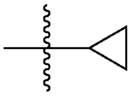 [SMILES: *C1CC1] | $NH_2$ |
| 96 | OPh | COOPh | $NH_2$ |
| 97 | SPh | COEt | $NH_2$ |
| 98 | CONHPr | Ph | $NH_2$ |
| 99 | CON(Me)$_2$ | Ph | $NH_2$ |
| 100 | 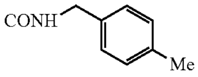 | Et | $NH_2$ |
| 101 | 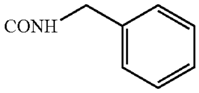 | Ph | $NH_2$ |
| 102 | 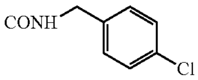 | COSMe | $NH_2$ |
| 103 | 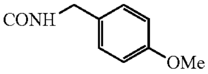 | Me | $NH_2$ |
| 104 | 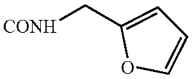 | Ph | $NH_2$ |

-continued

| | | | |
|---|---|---|---|
| 105 | 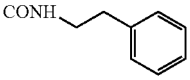 | Ph | $NH_2$ |
| 106 | 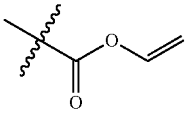 [SMILES: *C(=O)OC=C] | CONMePh | $NH_2$ |
| 107 | 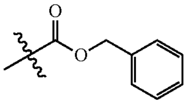 [SMILES: *C(=O)OCc1ccccc1] | Ph | $NH_2$ |
| 108 | 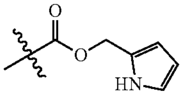 [SMILES: *C(=O)OCc1ccc[nH]1] | Et | $NH_2$ |
| 109 | 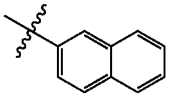 [SMILES: *c1ccc2ccccc2c1] | COOMe | $NH_2$ |
| 110 | $CH_3$ | $CH_3$ | 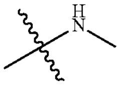 [SMILES: *NC] |
| 111 | $CH_3$ | $CH_3$ | 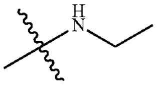 [SMILES: *NCC] |
| 112 | $CH_3$ | $CH_3$ | 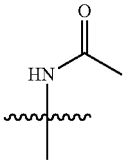 [SMILES: *NC(C)=O] |
| 113 | $CH_3$ | $CH_3$ | 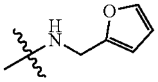 [SMILES: *NCc1ccco1] |
| 114 | $CH_3$ | $CH_3$ | 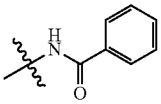 [SMILES: *NC(=O)c1ccccc1] |
| 115 | $CH_3$ | $CH_3$ | 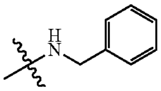 [SMILES: *NCc1ccccc1] |
| 116 | 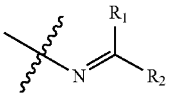 represents 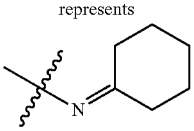 | | $NH_2$ |
| 117 | 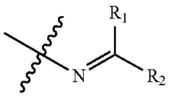 represents | | $NH_2$ |

-continued

| | | | |
|---|---|---|---|
| | 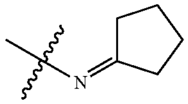 [SMILES: *N=C1CCCC1] | | |
| 118 | $CH_3$ | $CH_3$ | 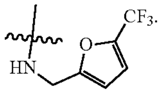 |

2. A method of preparing the pyridyloxy carboxylic oxime derivative according to claim 1, comprising:

reacting a compound of formula II with a compound of formula III to obtain a compound of formula I as follows:

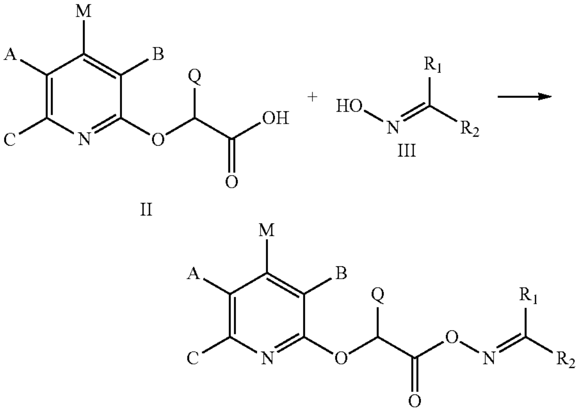

II III I

3. The method of claim 2, wherein the reaction is carried out in the presence of a dehydrant and a solvent.

4. The method of claim 3, wherein the dehydrant is DCC, and the solvent is one or more solvent selected from the group consisting of dichloromethane, dichloroethane, acetonitrile, N,N-dimethylformamide, N,N-dimethylacetamide, dimethyl sulfoxide, tetrahydrofuran, toluene, and xylene.

5. A herbicidal composition, comprising (i) at least one pyridyloxy carboxylic oxime derivative of claim 1; optionally further comprising (ii) at least one additional herbicide and/or safener, and/or (iii) at least one agrochemically acceptable formulation auxiliary.

6. A method for controlling a weed, comprising applying a herbicidally effective amount of at least one pyridyloxy carboxylic oxime derivative of claim 1 on a plant or in a weed area.

7. The method of claim 6, wherein the plant is rice; or the weed is a gramineous weed, a broad-leaved weed, or a cyperaceae weed.

8. The method of claim 6, wherein the plant is *japonica* rice or *indica* rice; or the weed is *Digitaria sanguinalis, Echinochlca crusgalli, Setaria viridis, Leptochloa chinensis, Monochoria Vaginalis, Galium spurium, Sagittaria trifolia, Murdannia triquetra, Cyperus iria*, or *Scirpus juncoides.*

9. A method for controlling a weed in a useful crop, comprising applying at least one pyridyloxy carboxylic oxime derivative of claim 1 to the useful crop or in a weed area.

10. The method of claim 8, wherein the useful crop is a genetically modified crop, or a crop treated by gene editing technology.

11. The method of claim 9, wherein the useful crop is rice; or the weed is a gramineous weed, a broad-leaved weed, or a cryperaceae weed.

12. The method of claim 9, wherein the useful crop is *japonica* rice or *indica* rice; or the weed is *Digitaria sanguinalis, Echinochloa crusgalli, Setaria viridis, Leptochloa chinensis, Monochoria Vaginalis, Galium spurium, Sagittaria trifolia, Murdannia triquetra, Cyperus iria*, or *Scirpus juncoides.*

* * * * *